United States Patent
Kirchmeier et al.

(10) Patent No.: US 11,167,032 B2
(45) Date of Patent: Nov. 9, 2021

(54) METHODS AND COMPOSITIONS FOR THERAPEUTIC AGENTS

(71) Applicant: Variation Biotechnologies Inc., Ottawa (CA)

(72) Inventors: Marc J. Kirchmeier, Harleysville, PA (US); David E. Anderson, Boston, MA (US)

(73) Assignee: Variation Biotechnologies Inc., Ottawa (CA)

(*) Notice: Subject to any disclaimer, the term of this patent is extended or adjusted under 35 U.S.C. 154(b) by 0 days.

(21) Appl. No.: 15/956,099

(22) Filed: Apr. 18, 2018

(65) Prior Publication Data

US 2018/0228899 A1 Aug. 16, 2018

Related U.S. Application Data

(62) Division of application No. 14/373,930, filed as application No. PCT/IB2013/000454 on Jan. 25, 2013, now abandoned.

(Continued)

(51) Int. Cl.
*A61K 39/12* (2006.01)
*A61K 47/14* (2017.01)
(Continued)

(52) U.S. Cl.
CPC .......... *A61K 47/14* (2013.01); *A61K 39/0015* (2013.01); *A61K 39/12* (2013.01);
(Continued)

(58) Field of Classification Search
None
See application file for complete search history.

(56) References Cited

U.S. PATENT DOCUMENTS

| | | |
|---|---|---|
| 3,952,097 A | 4/1976 | Levy |
| 4,024,241 A | 5/1977 | Levy |

(Continued)

FOREIGN PATENT DOCUMENTS

| | | |
|---|---|---|
| CA | 2258907 A1 | 12/1997 |
| CA | 2767392 A1 | 1/2011 |

(Continued)

OTHER PUBLICATIONS

Merriam-Webster, "Homogenize" found at https://www.merriam-webster.com/dictionary/homogenize (Year: 2020).*

(Continued)

*Primary Examiner* — M Franco G Salvoza
(74) *Attorney, Agent, or Firm* — Choate, Hall & Stewart LLP; Rolando Medina

(57) ABSTRACT

The present disclosure provides inter alia compositions that comprise therapeutic agents (e.g., live attenuated viral antigens, therapeutic proteins, etc.) and a lipid component. The lipid component may comprise or consist of different types of lipid or lipids as described herein. In some embodiments the therapeutic agents are thermolabile. The present disclosure also provides methods for preparing compositions, including the aforementioned compositions (e.g., melt methods and spray injection methods among others).

8 Claims, 4 Drawing Sheets

Related U.S. Application Data

(60) Provisional application No. 61/591,837, filed on Jan. 27, 2012.

(51) Int. Cl.

| | | |
|---|---|---|
| *A61K 39/395* | (2006.01) | |
| *C07K 16/32* | (2006.01) | |
| *A61K 39/00* | (2006.01) | |
| *A61K 39/165* | (2006.01) | |
| *A61K 39/20* | (2006.01) | |
| *A61K 39/295* | (2006.01) | |
| *A61K 47/24* | (2006.01) | |
| *A61K 47/28* | (2006.01) | |
| *C12N 7/00* | (2006.01) | |
| *A61K 9/127* | (2006.01) | |

(52) U.S. Cl.
CPC .......... *A61K 39/165* (2013.01); *A61K 39/20* (2013.01); *A61K 39/295* (2013.01); *A61K 39/39591* (2013.01); *A61K 47/24* (2013.01); *A61K 47/28* (2013.01); *C07K 16/32* (2013.01); *C12N 7/00* (2013.01); *A61K 9/1272* (2013.01); *A61K 2039/5254* (2013.01); *A61K 2039/55555* (2013.01); *A61K 2039/70* (2013.01); *C12N 2760/18434* (2013.01); *C12N 2760/18734* (2013.01); *C12N 2770/36234* (2013.01); *Y02A 50/30* (2018.01)

(56) References Cited

U.S. PATENT DOCUMENTS

| | | | |
|---|---|---|---|
| 4,349,538 A | 9/1982 | Levy | |
| 4,352,884 A | 10/1982 | Nakashima et al. | |
| 4,436,727 A | 3/1984 | Ribi | |
| 4,537,769 A | 8/1985 | Cerini | |
| 4,866,034 A | 9/1989 | Ribi | |
| 4,877,611 A | 10/1989 | Cantrell | |
| 4,894,228 A | 1/1990 | Purcell et al. | |
| 4,912,094 A | 3/1990 | Myers et al. | |
| 4,983,387 A | 1/1991 | Goldstein et al. | |
| 5,057,540 A | 10/1991 | Kensil et al. | |
| 5,160,669 A | 11/1992 | Wallach et al. | |
| 5,250,236 A | 10/1993 | Gasco | |
| 5,340,588 A | 8/1994 | Domb | |
| 5,393,527 A | 2/1995 | Malick et al. | |
| 5,393,530 A * | 2/1995 | Schneider ............ A61K 9/1278 264/4.3 | |
| 5,549,910 A | 8/1996 | Szoka, Jr. | |
| 5,567,434 A | 10/1996 | Szoka, Jr. | |
| 5,653,996 A | 8/1997 | Hsu | |
| 5,679,355 A | 10/1997 | Alexander et al. | |
| 5,817,318 A | 10/1998 | Sia et al. | |
| 5,853,753 A | 12/1998 | Maierhofer et al. | |
| 5,858,368 A | 1/1999 | Smith et al. | |
| 5,861,243 A | 1/1999 | Dietrich et al. | |
| 5,876,721 A | 3/1999 | Alexander et al. | |
| 5,879,703 A | 3/1999 | Fountain | |
| 5,910,306 A | 6/1999 | Alving et al. | |
| 5,919,480 A | 7/1999 | Kedar et al. | |
| 5,948,410 A | 9/1999 | Van Scharrenburg et al. | |
| 5,962,298 A | 10/1999 | Fiers et al. | |
| 5,977,081 A | 11/1999 | Marciani | |
| 6,005,099 A | 12/1999 | Davies et al. | |
| 6,080,725 A | 6/2000 | Marciani | |
| 6,090,392 A | 7/2000 | Berman | |
| 6,136,606 A | 10/2000 | Chatfield | |
| 6,180,110 B1 | 1/2001 | Funkhouser et al. | |
| 6,207,178 B1 | 3/2001 | Westesen et al. | |
| 6,235,888 B1 | 5/2001 | Pachuk et al. | |
| 6,248,363 B1 | 6/2001 | Patel et al. | |
| 6,287,570 B1 | 9/2001 | Foley | |
| 6,290,967 B1 | 9/2001 | Volkin et al. | |
| 6,303,347 B1 | 10/2001 | Johnson et al. | |
| 6,344,354 B1 | 2/2002 | Webster et al. | |
| 6,372,223 B1 | 4/2002 | Kistner et al. | |
| 6,383,806 B1 | 5/2002 | Rios | |
| 6,500,623 B1 | 12/2002 | Tung | |
| 6,503,753 B1 | 1/2003 | Rios | |
| 6,534,065 B1 | 3/2003 | Makin et al. | |
| 6,538,123 B2 | 3/2003 | Barban | |
| 6,541,003 B1 | 4/2003 | Smith | |
| 6,605,457 B1 | 8/2003 | Fiers et al. | |
| 6,635,246 B1 | 10/2003 | Barrett et al. | |
| 6,649,410 B2 | 11/2003 | Rios | |
| 6,653,130 B2 | 11/2003 | Rios | |
| 6,692,955 B1 | 2/2004 | Meredith et al. | |
| 6,706,859 B1 | 3/2004 | Sorensen | |
| 6,740,325 B1 | 5/2004 | Arnon et al. | |
| 6,743,900 B2 | 6/2004 | Burt et al. | |
| 6,764,840 B2 | 7/2004 | Johnson et al. | |
| 6,787,351 B2 | 9/2004 | Chen et al. | |
| 6,831,169 B2 | 12/2004 | Pachuk et al. | |
| 6,861,244 B2 | 3/2005 | Barrett et al. | |
| 6,991,929 B1 | 1/2006 | D'Hondt | |
| 7,052,701 B2 | 5/2006 | Barrett et al. | |
| 7,063,849 B1 | 6/2006 | Thibodeau et al. | |
| 7,067,134 B1 | 6/2006 | Kang et al. | |
| 7,192,595 B2 | 3/2007 | Arnon et al. | |
| 7,244,435 B2 | 7/2007 | Lai | |
| 7,262,045 B2 | 8/2007 | Schwartz et al. | |
| 7,316,813 B2 | 1/2008 | Eichhorn | |
| 7,348,011 B2 | 3/2008 | Guntaka et al. | |
| 7,361,352 B2 | 4/2008 | Birkett et al. | |
| 7,399,840 B2 | 7/2008 | Burt et al. | |
| 7,468,259 B2 | 12/2008 | Fiers et al. | |
| 7,494,659 B2 | 2/2009 | Katinger et al. | |
| 7,510,719 B2 | 3/2009 | Dang et al. | |
| 7,514,086 B2 | 4/2009 | Arnon et al. | |
| 7,527,800 B2 | 5/2009 | Yang et al. | |
| 7,537,768 B2 | 5/2009 | Luke et al. | |
| 9,610,248 B2 | 4/2017 | Anderson et al. | |
| 9,849,173 B2 | 12/2017 | Anderson et al. | |
| 9,907,746 B2 | 3/2018 | Anderson et al. | |
| 10,736,844 B2 | 8/2020 | Anderson et al. | |
| 2002/0164648 A1 | 11/2002 | Goins et al. | |
| 2003/0092145 A1 | 5/2003 | Jira et al. | |
| 2004/0011840 A1 | 1/2004 | Lovett | |
| 2004/0022840 A1 | 2/2004 | Nagy et al. | |
| 2004/0081688 A1 | 4/2004 | Del Curto et al. | |
| 2005/0042230 A1 | 2/2005 | Anderson et al. | |
| 2005/0095283 A1 | 5/2005 | Castor et al. | |
| 2005/0169979 A1 | 8/2005 | Michaeli et al. | |
| 2005/0214331 A1 | 9/2005 | Levy | |
| 2006/0121105 A1 | 6/2006 | Barenholz et al. | |
| 2006/0257852 A1 | 11/2006 | Rappuoli et al. | |
| 2007/0142315 A1 | 6/2007 | Forsbach et al. | |
| 2007/0224257 A1 | 9/2007 | Commander et al. | |
| 2007/0264273 A1 | 11/2007 | Barenholz et al. | |
| 2008/0057080 A1 | 3/2008 | Luke et al. | |
| 2008/0131466 A1 | 6/2008 | Reed et al. | |
| 2008/0145375 A1 | 6/2008 | Bembridge et al. | |
| 2008/0160089 A1 | 7/2008 | Vitiello et al. | |
| 2008/0181914 A1 | 7/2008 | Eichhorn | |
| 2008/0213461 A1 | 9/2008 | Gill et al. | |
| 2008/0268028 A1 | 10/2008 | Zurbriggen et al. | |
| 2008/0286353 A1 | 11/2008 | Gregoriadis | |
| 2009/0028903 A1 | 1/2009 | Hanon et al. | |
| 2009/0041809 A1 | 2/2009 | Emtage | |
| 2009/0081157 A1 | 3/2009 | Kornbluth et al. | |
| 2009/0081254 A1 | 3/2009 | Vajdy et al. | |
| 2009/0117141 A1 | 5/2009 | Torres et al. | |
| 2009/0130146 A1 | 5/2009 | Broeker | |
| 2009/0155309 A1 | 6/2009 | Friede et al. | |
| 2009/0181078 A1 | 7/2009 | Reed et al. | |
| 2009/0202620 A1 | 8/2009 | Turnell et al. | |
| 2009/0232883 A1 | 9/2009 | Yoshino | |
| 2010/0062071 A1 | 3/2010 | Loxley et al. | |
| 2010/0080844 A1 | 4/2010 | Bacon et al. | |
| 2010/0129392 A1 | 5/2010 | Shi et al. | |
| 2010/0226932 A1 | 9/2010 | Smith et al. | |
| 2011/0177163 A1 | 7/2011 | Diaz-Mitoma et al. | |
| 2012/0156240 A1 | 6/2012 | Anderson et al. | |

(56) References Cited

U.S. PATENT DOCUMENTS

| | | |
|---|---|---|
| 2012/0177683 A1 | 7/2012 | Anderson et al. |
| 2012/0276125 A1 | 11/2012 | Ast et al. |
| 2013/0108692 A1 | 5/2013 | Anderson et al. |
| 2013/0295165 A1 | 11/2013 | Anderson et al. |
| 2013/0323280 A1 | 12/2013 | Anderson et al. |
| 2014/0356399 A1 | 12/2014 | Anderson |
| 2015/0079077 A1 | 3/2015 | Kirchmeier et al. |
| 2018/0256723 A1 | 9/2018 | Anderson |

FOREIGN PATENT DOCUMENTS

| | | |
|---|---|---|
| CA | 2803282 A1 | 1/2011 |
| CN | 1169161 A | 12/1997 |
| CN | 101472563 A | 7/2009 |
| CN | 101574394 A | 11/2009 |
| EP | 0413637 A1 | 2/1991 |
| EP | 0 433242 A1 | 6/1991 |
| EP | 0489153 A1 | 6/1992 |
| EP | 729473 A1 | 9/1996 |
| EP | 1 129 723 A1 | 9/2001 |
| EP | 2 014 279 A1 | 1/2009 |
| GB | 2122204 A | 1/1984 |
| WO | WO-88/06882 A1 | 9/1988 |
| WO | WO-90/02965 A1 | 3/1990 |
| WO | WO-92/00081 A1 | 1/1992 |
| WO | WO-93/19781 A1 | 10/1993 |
| WO | WO-95/09651 A1 | 4/1995 |
| WO | WO-95/14026 A1 | 5/1995 |
| WO | WO-95/17210 A1 | 6/1995 |
| WO | WO-96/11280 A1 | 4/1996 |
| WO | WO-97/04768 A1 | 2/1997 |
| WO | WO-98/01139 A1 | 1/1998 |
| WO | WO-98/50399 A1 | 11/1998 |
| WO | WO-99/62500 A1 | 12/1999 |
| WO | WO-01/05374 A1 | 1/2001 |
| WO | WO-02/051390 A2 | 7/2002 |
| WO | WO-03/011223 A2 | 2/2003 |
| WO | WO-03/099195 A2 | 12/2003 |
| WO | WO-2005/117958 A1 | 12/2005 |
| WO | WO-2007/110776 A1 | 10/2007 |
| WO | WO-2008/153236 A1 | 12/2008 |
| WO | WO-2009/029695 A1 | 3/2009 |
| WO | WO-2009/091531 A2 | 7/2009 |
| WO | WO-2009/155489 A2 | 12/2009 |
| WO | WO-2010/033812 A1 | 3/2010 |
| WO | WO-2011/005769 A1 | 1/2011 |
| WO | WO-2011/005772 A1 | 1/2011 |
| WO | WO-2012/006367 A2 | 1/2012 |
| WO | WO-2012/006368 A2 | 1/2012 |
| WO | WO-2012/097346 A1 | 7/2012 |
| WO | WO-2012/097347 A1 | 7/2012 |
| WO | WO-2013/104995 A2 | 7/2013 |
| WO | WO-2013/111012 A2 | 8/2013 |

OTHER PUBLICATIONS

Alexopoulou et al., Preparation and characterization of lyophilized liposomes with incorporated quercetin, J Liposome Res. 16(1): 17-25 (2006).
Alpan et al., The role of dentritic cells, B cells, and M cells in gut-oriented immune responses, J. Immunol., 166(8): 4843-4852 (2001).
Anderson, R.J., Properties of Cholesterol Obtained from Different Sources, J. Biol. Chem., 71: 4007-418 (1927).
Andre et al., Inactivated candidate vaccines for hepatitis A, Prog. Med. Virol., 37: 72-95 (1990).
Bangham et al., Diffusion of univalent ions across the lamellae of swollen phospholipids, J. Mol. Biol. 13(1): 238-252 (1965).
Bennett, E. et al., Translational modifications to improve vaccine efficacy in an oral influenza vaccine, methods, 49: 322-327 (2009).
Bramwell, V. et al., Particulate delivery systems for vaccines: what can we expect?, The Journal of Pharmacy and Pharmacology, 58(6): 717-728 (2006).

CAS Registry 18656-38-7, Record for Dimyristoyl phosphatidylcholine, 2 pages (Nov. 16, 1984).
Chen et al., An overview of liposome lyophilization and its future potential, Journal of Controlled Release, 142: 299-311 (2010).
Chen et al., Research advances on Solid lipid nanoparticles as new drug carrier, Chinese Journal of Ethnomedicine and Ethnopharmacy, 2: 7-10 (2009).
Collins, et al., Non-Ionic Surfactant Vesicle Formulation of Stibogluconate for Canine Leishmaniasis, J. Pharm. Pharmacol. 42: 53 (1990).
Conacher, M. et al., Oral immunisation with peptide and protein antigens by formulation in lipid vesicles incorporating bile salts (bilosomes), Vaccine, 19(20-22): 2965-2974 (2001).
Cregg et al., High-Level Expression and Efficient Assembly of Hepatitis B Surface Antigen in the Methylotrophic Yeast, *Pichia pastoris*, Biotechnology, 5: 479-485 (1987).
Fattovich, G., Natural history of hepatitis B, J. Hepatol., 39 Suppl 1: S50-S58 (2003).
Field, et al., Inducers of interferon and host resistance. II. Multistranded synthetic polynucleotide complexes, Proc. Natl. Acad. Sci. USA, 58(3): 1004-1010 (1967).
Gnjatic, S. et al., TLR Agonists, The Cancer Journal, 16(4): 382-391 (2010).
Harford et al., Expression of hepatitis B surface antigen in yeast, Dev. Biol. Stand., 54: 125-130 (1983).
Hassan, Y. et al., Immune responses in mice induced by HSV-1 glycoproteins presented with ISCOMs or NISV delivery systems, Vaccine, 14(17-18): 1581-1589 (1996).
Hilleman MR., Critical overview and outlook: pathogenesis, prevention, and treatment of hepatitis and hepatocarcinoma caused by hepatitis B virus, Vaccine, 21(32): 4626-4649 (2003).
Hofland, H.E.J. et al., Nonionic Surfactant Vesicles: A Study of Vesicle Formation, Characterization and Stability, Journal of Colloid and Interface Science, 161(2): 366-376, Abstract Only , 2 pages (1993).
Huckriede, A. et al., The virosome concept for influenza vaccines, Vaccine, 23 Suppl 1:S26-38 (2005).
International Search Report for PCT/IB2013/000454, 4 pages (dated Jul. 17, 2013).
Israelachvili, J.N. et al., Physical Principles of Membrane Organization, Quarterly Reviews of Biophysics, 13(2): 121-200 (1980).
Jiang et al., Advances in non-ionic surfactant based vesicles, Chinese Journal of Modern Drug Application, 1:(11): 98-101 (2007). English Translation, pp. 1-8.
Jurk, et al., Modulating Responsiveness of Human TLR7 and 8 to Small Molecule Ligands With T-rich Phosphorothiate Oligodeoxynucleotides, Eur. J. Immunol., 36(7): 1815-26 (2006).
Kasrian and Deluca, The Effect of Tertiary Butyl Alcohol on the Resistance of the Dry Product Layer During Primary Drying, Pharm. Res., 12(4): 491-495 (1995).
Kasrian and Deluca, Thermal Analysis of the Tertiary Butyl Alcohol-Water System and Its Implications on Freeze-Drying, Pharm. Res., 12(4): 484-490 (1995).
Khmelnitsky et al., Denaturation capacity: a new quantitative criterion for selection of organic solvents as reaction media in biocatalysis, European Journal of Biochem., 198: 31-41 (1991).
Kirby, and Gregoriadis, Dehydration-Rehydration Vesicles: A Simple Method for Hight Yield Drug Entrapment in Liposomes, Biotechnology, 2(11):979-984 (1984).
Kumar, G.P. et al., Nonionic surfactant vesicular systems for effective drug delivery—an overview, Acta Pharmaceutica Sinica B, 1(4): 208-219 (2011).
Lasic, D.D., Novel Applications of Lipsomes, TIBTECH, 16:307-321 (1998).
Lavanchy, The Importance of Global Surveillance of Influenza, Vaccine, 17: S24-S25 (1999).
Levy et al., Inhibition of Tumor Growth by Polyinosinic-Polycytidylic Acid, Proc. Natl. Acad. Sci. USA, 62:357-361 (1969).
Li and Deng, A novel method for the preparation of liposomes: freeze drying of monophase solutions, J. Pharm. Sci., 93(6): 1403-1414 (2004).
Mann et al., Optimisation of a Lipid Based Oral Delivery System Containing A/Panama Influenza Haemagglutinin, Vaccine, 22: 2425-2429 (2004).

(56) References Cited

OTHER PUBLICATIONS

Manosroi, A. et al., Characterization of vesicles prepared with various non-ionic surfactants mixed with cholesterol, Colloids and Surfaces B: Biointerfaces, 30(1-2): 129-138 (2003).

Mao et al., Further evaluation of the safety and protective efficacy of live attenuated hepatitis A vaccine (H2-strain) in humans, Vaccine, 15(9): 944-947 (1997).

Martin, F. J. and MacDonald, R. C., Lipid vesicle-cell interactions. III. Introduction of a new antigenic determinant into erythrocyte membranes, The Journal of cell biology, 70: 515-526 (1976).

McAleer et al., Human hepatitis B vaccine from recombinant yeast, Nature, 307(5947): 178-180 (1984).

Miller et al., Hepatitis C virus shares amino acid sequence similarity with pestiviruses and flaviviruses as well as members of two plant virus supergroups, Proc. Natl. Acad. Sci., 87: 2057-2061 (1990).

Mowat, A.M., Dendritic cells and immune responses to orally administered antigens, Vaccine, 23(15): 1797-1799 (2005).

Mozafari, M.R., Nanomaterials and Nanosystems for Biomedical Applications, Springer, 1-159 (2007).

Oku, et al., Effect of serum protein binding on real-time trafficking of liposomes with different charges analyzed by positron emission tomography, Biochimica et Biophysica Acta, 1280:149-154 (1996).

Pick, Liposomes With a Large Trapping Capacity Prepared by Freezing and Thawing of Sonicated Phospholipid Mixtures, Arch. Biochem. Biophys, 212(1):186-194 (1981).

Provost et al., New findings in live, attenuated hepatitis A vaccine development, J. Med. Virol., 20(2): 165-175 (1986).

Russell, DG and Alexander, J., Effective immunization against cutaneous leishmaniasis with defined membrane antigens reconstituted into liposomes, Journal of Immunology, 140(4):1274-1279 (1988).

Salager, J-L., Surfactants—Types and Uses, FIRP Booklet #E300-A, Teaching Aid in Surfactant Science & Engineering, in English, Laboratory of Formulation, Interfaces, Rheology and Processes, Universidad de Los Andes, 2:1-50 (2002).

Schalk et al., Estimation of the Number of Infectious Measles Viruses in Live Virus Vaccines Using Quantitative Real-Time PCR, Journal of Virological Methods, 117:179-187 (2004).

Schubert et al., Solvent Injection as a New Approach for Manufacturing Lipid Nanoparticles—Evaluation of the Method and Process Parameters, European Journal of Pharmaceuticals and Biopharmaceutics, 55:125-131 (2003).

Senior, J. and Radomsky, M., Liposomes for Local Sustained Drug Release, Sustained-Release Injectable Products, Chapter 7: 137-180 (Published Sep. 30, 2005).

Szoka, Jr., F. and Papahadjopoulos, D., Comparative Properties and Methods of Preparaton of Lipid Vesicles (Liposomes)1, Ann. Rev. Viophys. Bioeng., 9:467-508 (1980).

Tarekegn, A. et al., Niosomes in Targeted Drug Delivery: Some Recent Advances, International Journal of Pharmaceutical Sciences and Research, 1(9): 1-8 (2010).

Uchegbu, I.F. and Vyas, S.P., Non-ionic surfactant based vesicles (niosomes) in drug delivery, in International Journal of Pharmaceuticals,172:33-70 (1998).

Valenzuela et al., Chemical synthesis of a gene for human epidermal growth factor urogastrone and its expression in yeast, Proc. Natl. Acad. Sci. USA, 80(24): 7461-7465 (1983).

Van Hal, D. A. et al., Preparation and Characterization of Nonionic Surfactant Vesicles, Journal of Colloid and Interface Science, 178(1): 263-273 (1996).

Vangala et al., A comparative study of cationic liposome and niosome-based adjuvant systems for protein subunit vaccines: characterisation, environmental scanning electron microscopy and immunisation studies in mice, Journal of Pharmacy and Pharmacology, 58:787-799, (2006).

Varun et al., Niosomes and Liposomes—Vesicular Approach Towards Transdermal Drug Delivery, International Journal of Pharmaceutical and Chemical Sciences, 1(3): 632-644 (2012).

Verma, S. et al., Nanoparticle vesicular systems: A versatile tool for drug delivery, Journal of Chemical and Pharmaceutical Research, 2(2):496-509 (2010).

Wagner et al., Liposome Technology for Industrial Purposes, J. Drug Delivery, vol. 2011, Article ID 591325 (9 pages) (2010).

Walde et al., Enzymes Inside Lipid Vesicles: Preparation, Reactivity and Applications, Biomol. Eng., 18:143-177 (2001).

Wang et al., Solvent Injection-Lyophilization of Tert-Butyl Alcohol/Water Cosolvent Systems for the Preparation of Drug-Loaded Solid Lipid Nanoparticles, Colloids and Surfaces B: Biointerfaces, 79:254-261 (2010).

Weiner et al., Variable and hypervariable domains are found in the regions of HCV corresponding to the flavivirus envelope and NS1 proteins and the pestivirus envelope glycoproteins, Virology 180(2): 842-848 (1991).

World Health Organization, The Immunological Basis for Immunization Series, Model 7: Measles (2009).

Written Opinion for PCT/IB2013/000454, 6 pages (dated Jul. 17, 2013).

Yan et al., Recent Advances in Liposome-Based Nanoparticles for Antigen Delivery, Polymer Reviews, 47(3): 329-344 (2007).

* cited by examiner

“METHODS AND COMPOSITIONS FOR THERAPEUTIC AGENTS

CROSS REFERENCE TO RELATED APPLICATIONS

The present application is a divisional application of U.S. application Ser. No. 14/373,930, filed on Jul. 23, 2014, which is the National Stage of International Application No. PCT/IB2013/000454, filed Jan. 25, 2013, which claims the benefit of U.S. provisional application Ser. No. 61/591,837, filed on Jan. 27, 2012, the contents of all of which are herein incorporated by reference in their entirety.

BACKGROUND

Most vaccines, including attenuated virus vaccines, lose potency over time and the rate of potency loss is temperature-dependent. Therefore, cold-chain systems have been established to ensure that the potency of vaccines is maintained by storing them under refrigerated conditions (in most cases between 2 and 8° C.) until the point of use. Establishing a cold chain for vaccine storage and distribution is a major undertaking and maintenance is difficult. It is also apparent that, despite best efforts, cold chains do not always function as intended for many reasons, such as improperly maintained or outdated refrigeration equipment, power outages resulting in equipment failure, poor compliance with cold-chain procedures and inadequate monitoring. The result is that vaccines in the cold chain are often subjected to temperature excursions (i.e., temperatures outside of the target range).

Other therapeutic agents, e.g., certain therapeutic proteins also lose potency when exposed to high temperatures. There therefore remains a need in the art for improved compositions and methods that allow these therapeutic agents to be stable and retain potency when exposed to high temperatures.

SUMMARY

The present disclosure provides inter alia compositions that comprise therapeutic agents (e.g., live attenuated viral antigens, therapeutic proteins, etc.) and a lipid component. The lipid component may comprise or consist of different types of lipid or lipids as described herein. In some embodiments the therapeutic agents are thermolabile.

In one aspect, the lipid component consists of one or more non-ionic surfactants. In some embodiments, the lipid component in these compositions consists of a single non-ionic surfactant (e.g., MPG).

In another aspect, the lipid component consists of one or more non-ionic surfactants and one or more steroids. In some embodiments, the lipid component in these compositions consists of a single non-ionic surfactant (e.g., MPG) and a single steroid (e.g., cholesterol).

In another aspect, the lipid component comprises one or more lipids that combine to form vesicles (i.e., "vesicular compositions"). In some embodiments, the lipids are combined to form vesicles in the absence of therapeutic agent and then admixed with the therapeutic agent (i.e., the compositions include "pre-formed vesicles"). In some of these embodiments, the lipids comprise a non-ionic surfactant, a steroid and an ionic amphiphile. Vesicular compositions prepared in accordance with these embodiments may include any ionic amphiphile including any of the exemplary ionic amphiphiles that are described herein. In some embodiments, the lipids are combined to form vesicles in the presence of therapeutic agent. Vesicular compositions prepared in accordance with these embodiments may include any of the exemplary phosphoglycerides that are described herein as an ionic amphiphile. In some embodiments, the lipid component in these vesicular compositions consists of a single non-ionic surfactant (e.g., MPG), a single steroid (e.g., cholesterol) and a single ionic amphiphile (e.g., DCP or DPPG). In some embodiments, the lipid component in these vesicular compositions consists of a single non-ionic surfactant (e.g., MPG), a single steroid (e.g., cholesterol) and a single ionic amphiphile (e.g., DCP) and the vesicles are pre-formed. In some embodiments, the lipid component in these vesicular compositions consists of a non-ionic surfactant (e.g., MPG), a steroid (e.g., cholesterol) and a phosphoglyceride as the ionic amphiphile (e.g., DPPG) and the vesicles are pre-formed or formed in the presence of therapeutic agent.

The present disclosure also provides methods for preparing compositions, including the aforementioned compositions (e.g., melt methods and spray injection methods among others).

DEFINITIONS

Figure 1:
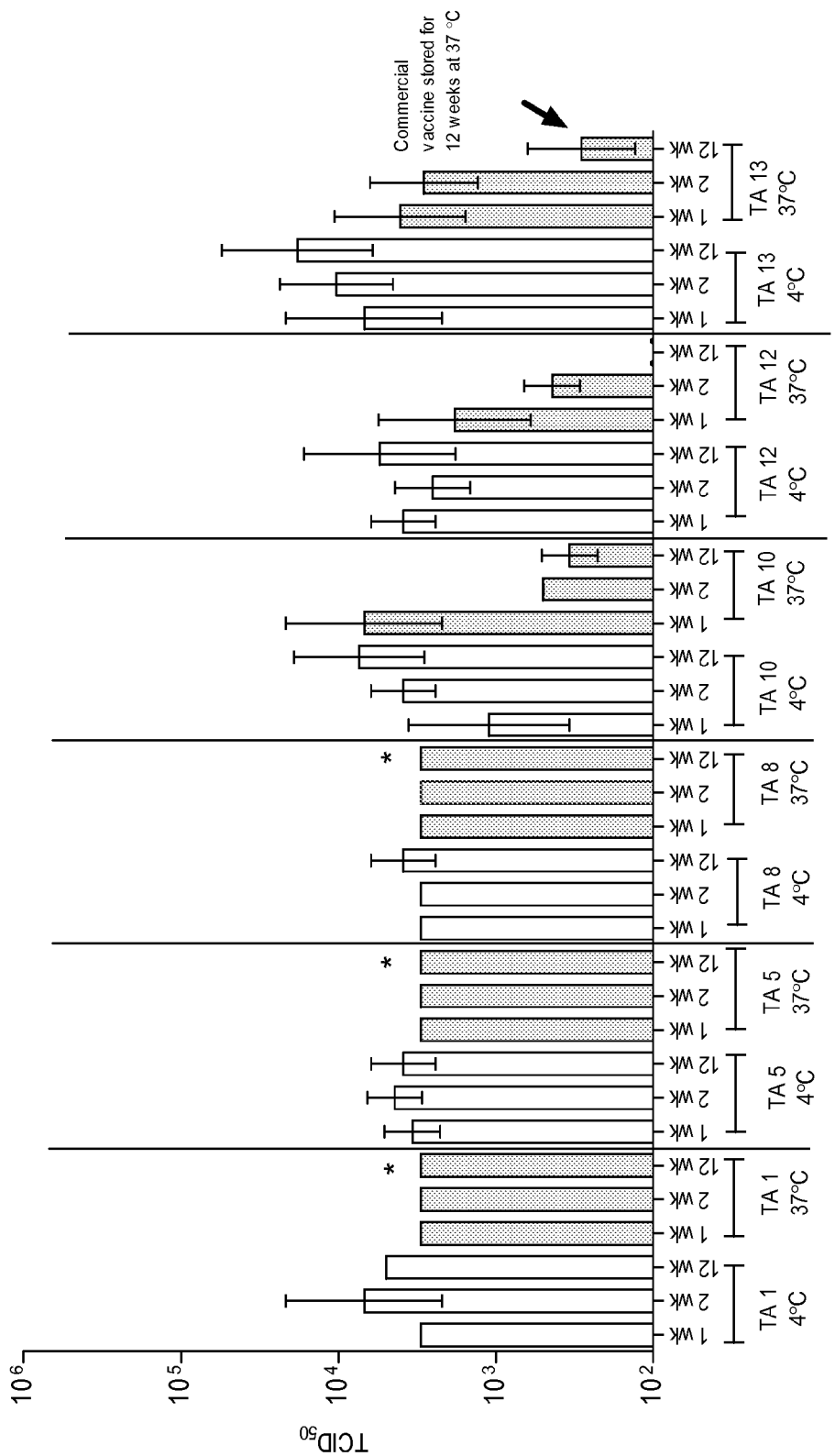
FIG. 1 shows exemplary results from a measles potency assay ($TCID_{50}$) that was performed using different reformulated M-M-R-II® vaccines (formulated with 25 mg/ml lipid) that had been stored at about 4° C. and about 37° C. for 1, 2 and up to 12 weeks.

Throughout the present disclosure, several terms are employed that are defined in the following paragraphs.

As used herein, the term "antigen" or "viral antigen" refers to a substance containing one or more epitopes that can be recognized by an antibody. In some embodiments, an antigen can be a virus. The term "antigen" encompasses inter alia attenuated and inactivated viruses. In some embodiments, an antigen may be an "immunogen."

As used herein, the term "immune response" refers to a response elicited in an animal. An immune response may refer to cellular immunity, humoral immunity or may involve both. An immune response may also be limited to a part of the immune system. For example, in some embodiments, an immunogenic composition may induce an increased IFNγ response. In some embodiments, an immunogenic composition may induce a mucosal IgA response (e.g., as measured in nasal and/or rectal washes). In some embodiments, an immunogenic composition may induce a systemic IgG response (e.g., as measured in serum).

As used herein, the term "immunogenic" means capable of producing an immune response in a host animal against a non-host entity (e.g., a viral antigen). In some embodiments, this immune response forms the basis of the protective immunity elicited by a vaccine against a specific infectious organism (e.g., a virus).

As used herein, the terms "therapeutically effective amount" refer to the amount sufficient to show a meaningful benefit in a subject being treated. The therapeutically effective amount of a composition may vary depending on such factors as the desired biological endpoint, the nature of the composition, the route of administration, the health, size and/or age of the subject being treated, etc.

As used herein, the term "treat" (or "treating", "treated", "treatment", etc.) refers to the administration of a composition to a subject who has a disease, a symptom of a disease or a predisposition toward a disease, with the purpose to alleviate, relieve, alter, ameliorate, improve or affect the disease, a symptom or symptoms of the disease, or the predisposition toward the disease. In some embodiments, the term "treating" refers to the vaccination of a subject.

DETAILED DESCRIPTION OF SOME EMBODIMENTS

1. Compositions

The present disclosure provides inter alia compositions that comprise therapeutic agents and a lipid component. As used herein the term "lipid component" encompasses all lipids that are present in the composition. The lipid component may comprise or consist of different types of lipid or lipids as described herein.

Lipid Component

In one aspect, the lipid component consists of one or more non-ionic surfactants. In some embodiments, the lipid component consists of a single non-ionic surfactant. Without limitation, examples of suitable non-ionic surfactants include ester-linked surfactants based on glycerol. Such glycerol esters may comprise one of two higher aliphatic acyl groups, e.g., containing at least ten carbon atoms in each acyl moiety. Non-ionic surfactants based on such glycerol esters may comprise more than one glycerol unit, e.g., up to 5 glycerol units. Glycerol monoesters may be used, e.g., those containing a $C_{12}$-$C_{20}$alkanoyl or alkenoyl moiety, for example caproyl, lauroyl, myristoyl, palmitoyl, oleyl or stearoyl. An exemplary non-ionic surfactant is 1-monopalmitoyl glycerol (MPG). Ether-linked surfactants may also be used as non-ionic surfactants. For example, ether-linked surfactants based on glycerol or a glycol having a lower aliphatic glycol of up to 4 carbon atoms, such as ethylene glycol, are suitable. Non-ionic surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monocetyl glycerol ether and diglycolcetyl ether.

In another aspect, the lipid component consists of one or more non-ionic surfactants and one or more steroids (e.g., a sterol such as cholesterol). In some embodiments, the lipid component consists of a single non-ionic surfactant (e.g., MPG) and a single steroid (e.g., cholesterol). In some embodiments, the non-ionic surfactant(s) and steroid(s) are present in the composition in a molar ratio in the range of about 6:4 to about 4:4, e.g., about 5:4.

In another aspect, the lipid component comprises one or more lipids that combine to form vesicles (i.e., "vesicular compositions").

In some embodiments, the lipids are combined to form vesicles in the absence of therapeutic agent and then admixed with the therapeutic agent (i.e., the compositions include "pre-formed vesicles"). In some of these embodiments, the lipids comprise a non-ionic surfactant, a steroid (e.g., a sterol such as cholesterol) and an ionic amphiphile. Vesicular compositions prepared in accordance with these embodiments may include any ionic amphiphile including any of the exemplary ionic amphiphiles that are described below.

In some embodiments, the lipids are combined to form vesicles in the presence of therapeutic agent. Vesicular compositions prepared in accordance with these embodiments may include any of the exemplary phosphoglycerides that are described below as an ionic amphiphile.

Exemplary ionic amphiphiles may include, but are not limited to, acidic materials such as higher alkenoic and alkenoic acids (e.g., palmitic acid, oleic acid) or other compounds containing acidic groups including phosphates such as dialkyl phosphates (e.g., dicetylphospate or DCP, or phosphatidic acid or phosphatidyl serine) and sulphate monoesters such as higher alkyl sulphates (e.g., cetylsulphate), may all be used for this purpose.

As noted, above, in some embodiments, a phosphoglyceride (also known as a glycerophospholipid) can be used as an ionic amphiphile. Phosphoglycerides can be plasmalogens, phosphatidates (such as phosphatidylethanoamines, phosphatidylcholines), phosphatidylchonlines, or the like. Exemplary phosphoglycerides include, but are not limited to diphosphatidyl glycerol (DPPG); 1,2-Dipalmitoyl-sn-glycero-3-phospho-L-serine (DPPS); 1,2-Distearoyl-sn-glycero-3-phosphatidylcholine (DSPC); 1,2-Distearoyl-sn-glycero-3-phosphoethanolamine (DSPE); phosphatidylcholine dipalmitoyl (DPPC) and derivatives thereof.

In some embodiments, the lipid component in these vesicular compositions consists of a single non-ionic surfactant (e.g., MPG), a single steroid (e.g., cholesterol) and a single ionic amphiphile (e.g., DCP or DPPG). In some embodiments, the lipid component in these vesicular compositions consists of a single non-ionic surfactant (e.g., MPG), a single steroid (e.g., cholesterol) and a single ionic amphiphile (e.g., DCP) and the vesicles are pre-formed. In some embodiments, the lipid component in these vesicular compositions consists of a non-ionic surfactant (e.g., MPG), a steroid (e.g., cholesterol) and a phosphoglyceride as the ionic amphiphile (e.g., DPPG) and the vesicles are pre-formed or formed in the presence of therapeutic agent.

In some embodiments, the non-ionic surfactant(s) and steroid are present in these vesicular compositions in a molar ratio in the range of about 6:4 to about 4:4: e.g., about 5:4. In some embodiments, the non-ionic surfactant(s) and ionic amphiphile are present in these vesicular compositions in a molar ratio in the range of about 6:1 to about 4:1: e.g., about 5:1. In some embodiments, the steroid and ionic amphiphile are present in these vesicular compositions in a molar ratio in the range of about 5:1 to about 3:1: e.g., about 4:1.

In certain embodiments, a lipid concentration of at least about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90 or 95 mg/ml is achieved. In certain embodiments, the lipid concentration is in a range of about 5 mg/ml to about 10, 11, 12, 13, 14, 15, 16, 17, 18, 19, 20, or 25 mg/ml. In certain embodiments, the lipid concentration is in a range of about 5, 6, 7, 8, 9, 10, 11, 12, 13, 14, 15 mg/ml to about 30 mg/ml. In certain embodiments, the lipid concentration is in a range of about 5 mg/ml to about 50 mg/ml, about 5 mg/ml to about 25 mg/ml, about 10 mg/ml to about 50 mg/ml, about 10 mg/ml to about 30 mg/ml, or about 10 mg/ml to about 50 mg/ml.

In some embodiments, the compositions described herein do not comprise a transport enhancing molecule which facilitates the transport of lipid-like molecules across mucosal membranes. In some embodiments, the compositions do not comprise a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the compositions do not comprise acyloxylated amino acids, such as acylcarnitines and salts thereof, and palmitoylcarnitines.

Therapeutic Agents

The present disclosure encompasses the uses of different types of therapeutic agents. In some embodiments, these agents are thermolabile. As used herein, the terms "thermolabile agent" refer to agents that loses potency when exposed to certain elevated temperatures. In some embodiments, exposure of a thermolabile agent to elevated temperatures destroys over 20% of the potency of the antigen (e.g., over 30%, over 40%, over 50% or more) as measured in a potency assay (e.g., based on an $IC_{50}$ or $EC_{50}$ value) as compared to the un-manipulated agent. In some embodiments, a thermolabile antigen loses potency at temperatures above 30° C. (e.g., above 35° C., above 40° C., above 45° C., or above 50° C.). In some embodiments, storage of a thermolabile agent at one of these elevated temperatures for more than 3 minutes (e.g., 5 minutes, 10 minutes, 15 minutes or more) destroys over 20% of the potency (e.g., over 30%, over 40%, over 50% or more) as measured in a potency assay (e.g., based on an $IC_{50}$ or $EC_{50}$ value) as compared to the un-manipulated agent. It is however to be understood that the methods and compositions of the present disclosure are not limited to thermolabile agents and that, in some embodiments, the methods or compositions may also involve more stable agents including traditional small molecule therapeutics.

Viral Antigens—Measles, Mumps, Rubella and Varicella Viral Antigens

Measles, mumps and rubella are three common childhood diseases that are caused by viral infection (by measles virus (a paramyxovirus), mumps virus (a paramyxovirus), and rubella virus (a togavirus), respectively). Measles, mumps and rubella infections may cause serious medical complications which may lead to death. Measles is an infection of the respiratory system and causes symptoms including fever, cough, runny nose, and general rash, and commonly leads to complications such as pneumonia and encephalitis. Mumps is an infection that causes symptoms including inflammation, fever, headache and orchitis, and can lead to complications such as aseptic meningitis and deafness. Rubella, commonly known as German measles, generally causes mild symptoms, although infection of a mother during pregnancy can be quite serious.

Vaccines against measles, mumps and rubella are produced from live attenuated viruses which have been propagated in cell substrates. Each component of MMR vaccine is initially prepared in the monovalent form, each of which is then mixed together to produce a trivalent form in which the component virus population is present in a well defined quantity sufficient to induce an effective immune response in a vaccine recipient. The marketed MMR vaccines are presented as a lyophilized vial, which has to be kept at 2-8° C. for no more than 3 years as per the licensure indications. However several factors including stabilizer composition, storage conditions and residual moisture can affect the thermal stability of the lyophilized vaccine. The World Health Organization (WHO) recommends tissue culture infective doses ($TCID_{50}$) assay using Vero cells for evaluating potency of live measles virus in the vaccine. However, the potency measurements may vary depending on the method of determination, the laboratory, and the conditions at the time of the test.

WHO has set up minimum requirements for vaccine stability in freeze dried form as well as when reconstituted as a liquid solution prior to administration. In the freeze dried state, current measles vaccines must retain a minimum potency of at least 3.0 $\log_{10}$ virus particles per human dose after exposure to a temperature of 37° C. for at least one week and the virus titre dose not decrease by more than 1.0 $\log_{10}$ during incubation. However, reconstituted measles vaccines quickly lose potency at exposure to room temperatures. At 22° C. to 25° C. the vaccine loses approximately 50% of potency in one hour. At temperatures over 37° C. the vaccine is inactivated within one hour (The Immunological Basis for Immunization Series, Module 7: Measles (WHO/EPI/GEN/93.17).

Several attenuated measles, mumps and rubella (MMR) vaccines are currently licensed and have been successful in reducing the incidence of viral infection, and may be used in accordance with the present disclosure.

In some embodiments, the compositions and methods of the present disclosure may be used with one or more antigens included in a vaccine that is licensed or under development. Table 1 is a non-limiting list of vaccines that are licensed or under development for measles, mumps, rubella and varicella infections.

TABLE 1

| Vaccine | Disease |
|---|---|
| Attenuvax ® | Measles |
| Diplovax HDC 4.0 ® | Measles |
| Morbilvax ® | Measles |
| Rimevax ® | Measles |
| M-R-Vax, M-R-VaxII ® | Measles and Rubella |
| Moru-Viraten ® | Measles and Rubella |
| M-M-R Vax ® | Measles, Mumps and Rubella |
| M-M-R-II ® | Measles, Mumps and Rubella |
| M-M-RvaxPRO ® | Measles, Mumps and Rubella |
| Priorix ® | Measles, Mumps and Rubella |
| Trimovax ® | Measles, Mumps and Rubella |
| Triviraten Berna ® | Measles, Mumps and Rubella |
| ProQuad ® | Measles, Mumps, Rubella and Varicella |
| Mumpsvax ® | Mumps |
| Rubilin ® | Mumps and Rubella |
| Meruvax II ® | Rubella |
| Ervevax ® | Rubella |
| R-Vac ® | Rubella |
| Varivax ® | Varicella |

In the following sections we discuss these and other exemplary viral antigens that could be used in compositions or methods of the present disclosure.

In the United States, a measles, mumps and rubella (MMR) vaccine was first licensed in 1971, with a second dose of the vaccine introduced in 1989. In general, in countries where childhood MMR vaccination is routine, the incidence of measles, mumps and rubella has dramatically decreased (e.g., by more than 99% in 1995 as compared to the number of cases in 1941).

Several attenuated measles, mumps and rubella (MMR) vaccines are currently licensed. For example, M-M-R-II® is developed and manufactured by Merck & Co., Inc. M-M-R-II® contains a sterile lyophilized preparation of (1) Attenuvax® (Measles Virus Vaccine Live) an attenuated line of measles virus, (2) Mumpsvax® (Mumps Virus Vaccine Live) a strain of mumps virus propagated in chick embryo cell culture, and (3) Meruvax II® (Rubella Virus Vaccine Live) an attenuated strain of rubella virus. Each 0.5 mL dose contains not less than 1,000 $TCID_{50}$ (50% tissue culture infectious dose) of measles virus, not less than 5,000 $TCID_{50}$ of mumps virus, and not less than 1,000 $TCID_{50}$ of rubella virus. Upon reconstitution, M-M-R-TI® (as with other licensed MMR vaccines) is typically administered subcutaneously. Although one dose of M-M-R-II® in children over 12 months of age generally induces the production of neutralizing antibodies, some patients fail to seroconvert after the first dose. Accordingly, a second booster is recommended, especially prior to elementary school entry, in order to seroconvert those who did not respond to the first dose. In order to ensure that there is no loss of potency of the M-M-R-II® vaccine, it must be maintained at a temperature of 10° C. or colder during shipment, maintained at a temperature of 2° C. to 8° C. during storage in a lyophilized state, and used within 8 hours after reconstitution.

Another example of an MMR vaccine, PROQUAD® which also contains a Varicella component has been licensed and sold in the Unites States by Merck, although production is currently suspended. PROQUAD® is administered once in children over 12 months of age, with an optional booster administered at least three months later.

In one aspect, the present disclosure provides immunogenic compositions that include an attenuated or inactivated virus. It is to be understood that immunogenic compositions provided by the present disclosure may include one or more components of an MMR vaccine (e.g., measles, mumps, or rubella virus, or a combination thereof). In some embodiments, immunogenic compositions include a varicella virus component (e.g., alone, such as with VARIVAX®, or in combination with other virus components, such as with PROQUAD®).

As mentioned above, all known licensed MMR vaccines include attenuated viruses. It is to be understood that any one of these licensed vaccines may be used as described herein to produce an immunogenic composition. For example, commercial M-M-R-II® may be used to produce an immunogenic composition. In some embodiments, licensed vaccines are first purified (e.g., to remove alum adjuvant or other reagents in the vaccine). In some embodiments, licensed vaccines are not purified prior to formulation as described herein.

As is well known in the art, the advantage of an attenuated virus lies in the potential for higher immunogenicity which results from its ability to replicate in vivo without causing a full infection. One method which has been used in the art to prepare attenuated viruses is viral adaptation which involves serially passing a viral strain through multiple cell cultures. Over time the strain mutates and attenuated strains can then be identified. For example, in preparing M-M-R-II®, an attenuated strain of measles virus is propagated in chick embryo cell culture, a B level strain of mumps is propagated in chick embryo cell culture, and an attenuated strain of rubella is propagated in human diploid lung fibroblasts. In some embodiments the virus may be passed through different cell cultures.

It will be appreciated that any measles, mumps, and/or rubella virus strain may be used, e.g., without limitation any of the following strains which have been described in the art:

Measles virus Enders' attenuated Edmonston strain (AttA)
Measles virus attenuated AIK-C strain
Mumps virus Jeryl Lynn (B-level) strain
Mumps virus Leningrad Zagreb strain
Mumps virus Urabe Am 9 strain
Rubella virus Wistar RA 27/3 strain
Rubella virus Giguere; 1964 United States
- Rubella virus HPV-77; 1961 United States
- Rubella virus Judith; 1963 Liverpool U.K.
- Rubella virus KO-1; 1967 Kochi, Japan While all currently licensed MMR vaccines include attenuated viruses, alternative vaccines which include inactivated viruses may be used in accordance with the present disclosure. In some embodiments, an immunogenic composition may comprise such an inactivated virus. It will be appreciated that any method may be used to prepare an inactivated virus. In general, these methods will involve propagating a virus in a host cell, lysing the host cell to release the virus, isolating and then inactivating the virus. The virus is typically harvested from cell cultures and screened for infectious dosage as well as for the absence of adventitious agents. Chemical treatment of the virus (e.g., formalin, formaldehyde, among others) is commonly used to inactivate the virus. However, it is to be understood that other techniques could be used, e.g., treatment with chlorine, exposure to high temperatures, etc.

Viral Antigens—Others

Table 2 is a non-limiting list of other live attenuated vaccines that are licensed or under development. It is to be understood that compositions provided by the present disclosure may include one or more components of these vaccines.

TABLE 2

| Vaccine | Disease |
|---|---|
| DA2PPC | Canine Distemper, Adenovirus type 2, Parainfluenza, Canine Parvovirus, and Canine Coronavirus |
| RotaTeq ® | Rotavirus |
| Rotarix ® | Rotavirus |
| Zostavax ® | Shingles |
| Dryvax ® | Smallpox and Monkeypox |
| YF-Vax ® | Yellow Fever |
| PRRS Virus Vaccine | Porcine Reproductive and Respiratory Syndrome Virus |
| PR Virus Vaccine | PseudoRabies Virus |

Canine distemper is a disease caused by viral infection by canine distemper virus, which is a paramyxovirus that is closely related to measles virus. Canine distemper virus may cause serious medical conditions affecting a variety of mammalian species including dogs, weasels, skunks, hyenas, raccoons, and non-domestic felines. Canine distemper infection may causes symptoms including fever, anorexia, runny nose, and eye discharge, and commonly leads to complications such as pneumonia and encephalitis. An attenuated canine distemper vaccine has been licensed, including a multivalent DA2PPC vaccine, which protects against canine distemper (D), adenovirus type 2 (A2), parainfluenza (P), canine parvovirus (P) and canine coronavirus (C). It is to be understood that immunogenic compositions provided by the present disclosure may include one or more components of DA2PPC (e.g., a canine distemper virus antigen).

Rotavirus infection leads to rotavirus gastroenteritis, which can be especially severe in infants and young children. Licensed live attenuated vaccines for treatment of rotavirus infection include RotaTeq® and Rotarix®. RotaTeq® is indicated for the prevention of rotavirus gastroenteritis caused by the G1, G2, G3, and G4 serotypes of the virus. RotaTeq® is administered orally in a three-dose series to infants between the ages of 6 to 32 weeks. Each 2 ml dose of RotaTeq® contains a live reassortant virus, containing G1, G2, G3, G4, and P1A and contains a minimum of $2.0-2.8 \times 10^6$ infectious units (IU). Rotarix® is indicated for the prevention of rotavirus gastroenteritis caused by G1, G3, G4, and G9 serotypes of the virus. Rotarix® is administered orally in a two-dose series to infants between the ages of 6 weeks and 24 weeks of age. Each 1 ml dose of Rotarix® contains a minimum of $10^6$ $CCID_{50}$ of live, attenuated human G1P rotavirus.

Shingles is a viral infection of the nerve roots, which typically causes pain and rash on one side of the body. Shingles is most common in older adults and people with weak immune systems. A licensed virus for treatment of shingles caused by herpes zoster virus infection is Zostavax®, which is a lyophilized preparation of the Oka/Merck strain of live, attenuated varicella-zoster virus. Zostavax® is indicated for subcutaneous administration and is indicated for individuals 60 years of age and older. Each 0.65 ml dose of Zostavax® contains at least 19,400 pfu of live, attenuated virus.

Another example of a licensed live attenuated vaccine is DRYVAX®, which is a live-virus preparation of vaccinia virus for treatment of smallpox virus infection. DRYVAX® is prepared from calf lymph which is purified, concentrated, and dried by lyophilization. The reconstituted vaccine has been shown to contain not more than 200 viable bacterial organisms per ml. DRYVAX® is intended for multiple-puncture use, i.e., administration of the vaccine into the superficial layers of the skin using a bifurcated needle. Typically, vaccination with DRYVAX® results in viral multiplication, immunity, and cellular hypersensitivity. With the primary vaccination, a papule appears at the site of vaccination on about the 2nd to 5th day. This becomes a vesicle on the 5th or 6th day, which becomes pustular, umbilicated, and surrounded by erythema and induration. The maximal area of erythema is attained between the 8th and 12th day following vaccination (usually the 10th). The erythema and swelling then subside, and a crust forms which comes off about the 14th to 21st day. At the height of the primary reaction known as the Jennerian response, there is usually regional lymphadenopathy and there may be systemic manifestations of fever and malaise. Primary vaccination with DRYVAX® at a potency of 100 million pock-forming units (pfu)/ml has been shown to elicit a 97% response rate by both major reaction and neutralizing antibody response in children.

Yet another example of a licensed live attenuated vaccine is YF-VAX® for treatment of yellow fever virus infections. YF-VAX® is prepared by culturing the 17D strain of yellow fever virus in living avian leukosis virus-free chicken embryos. YF-VAX® is lyophilized and sealed under nitrogen for storage and is reconstituted immediately prior to use. YF-VAX® is formulated to contain not less than 5.04 $Log_{10}$ pfu per 0.5 ml dose. Typically, immunity to yellow fever develops by the tenth day after primary vaccination with YF-VAX®. Although it has been demonstrated that yellow fever vaccine immunity can persist for at least 30-35 years, and in some cases for life, booster vaccinations are required at intervals of 10 years in order to boost antibody titer.

Porcine reproductive and respiratory syndrome virus (PRRSV), also known as blue-ear pig disease is a virus that causes a disease of pigs, called porcine reproductive and respiratory syndrome (PRRS). This economically important, pandemic disease causes reproductive failure in breeding stock and respiratory tract illness in young pigs. A live attenuated vaccine has been developed to prevent PRRS.

Pseudorabies is a viral disease in swine that is endemic in most parts of the world. It is caused by *Suid herpesvirus* 1 (SuHV-1), which is also called Pseudorabies virus (PRV) and is also known as Aujeszky's disease, and in cattle as mad itch. Other domestic and wild mammals, such as cattle, sheep, goats, cats, dogs, and raccoons, are also susceptible where the disease is usually fatal. Research on PRV in pigs has pioneered animal disease control with live attenuated vaccines. Although the word "pseudorabies" means "false rabies," or "rabies-like," it is a misnomer. Pseudorabies is related to the herpes virus, not the rabies virus.

Therapeutic Proteins

Many therapeutic proteins (including a number of thermolabile therapeutic proteins) are currently licensed or in development and may be used in accordance with the present disclosure.

As used herein, the term "protein" refers to a polymer of amino acids. In some embodiments, proteins may include moieties other than amino acids (e.g., may be glycoproteins, proteoglycans, lipoproteins, etc.) and/or may be otherwise processed or modified. Those of ordinary skill in the art will appreciate that a "protein" can be a complete polypeptide chain as produced by a cell (with or without a signal sequence), or can be a portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art.

Therapeutic proteins are proteins that are either extracted from human cells or engineered in the laboratory for pharmaceutical use. The majority of therapeutic proteins are recombinant human proteins manufactured using non-human mammalian cell lines that are engineered to express certain human genetic sequences to produce specific proteins. Recombinant proteins are an important class of therapeutics used, for example, to replace deficiencies in critical blood borne growth factors and to strengthen the immune system to fight cancer and infectious disease. Therapeutic proteins are also used to relieve patients' suffering from many conditions, including various cancers (treated by monoclonal antibodies and interferons), heart attacks, strokes, cystic fibrosis and Gaucher's disease (treated by enzymes and blood factors), diabetes (treated by insulin), anemia (treated by erythropoietins), and hemophilia (treated by blood clotting factors).

The FDA has approved 75 therapeutic proteins, also known as biopharmaceuticals, and there are more than 500 additional proteins under development. Therapeutic biological products currently under regulatory review include: monoclonal antibodies, cytokines, growth factors, enzymes, immunomodulators; and thrombolytics and proteins intended for therapeutic use that are extracted from animals or microorganisms, including recombinant versions of these products and other non-vaccine therapeutic immunotherapies.

In some embodiments, a therapeutic protein is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules, and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibodies may be of any type (e.g., IgA, IgD, IgE, IgG, IgM).

In some embodiments, a therapeutic protein is an antibody fragment. As used herein, an "antibody fragment" includes a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

Some exemplary therapeutic proteins that may be used in accordance with the present disclosure are listed in Table 3 below. One exemplary therapeutic protein is Herceptin® (trastuzumab), a humanized monoclonal antibody that binds to the extracellular component of the Her2/neu receptor, a 185 kDa transmembrane oncoprotein that is overexpressed in approximately 20 to 25% of breast cancer patients. The antibody and other biosimilars are designed to express the human Fc-Gamma-1 isotype to increase both Complement Dependent Cytotoxicity (CDC) and Antibody Dependent Cellular Cytotoxicity (ADCC) function of the antibody. The Fab-related function of trastuzumab enables high affinity binding to the extracellular domain of the Her2/neu receptor which inhibits cell proliferation and prevents angiogenesis.

Polynucleotides

Polynucleotides may also be used in accordance with the present disclosure. As used herein, the term "polynucleotide" refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

In some embodiments, a polynucleotide used in accordance with the present disclosure is DNA, RNA, an aptamer, shRNA, siRNA, miRNA, and/or antisense RNA, or antagomir RNA.

Polysaccharides

Polysaccharides may also be used in accordance with the present disclosure. As used herein, the term "polysaccharide" refers to a polymer of sugars. The polymer may include natural sugars (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified sugars (e.g., 2'-fluororibose, 2'-deoxyribose, and hexose).

Small Molecules

As noted previously, while the methods and compositions of the present disclosure are thought to be particularly useful for thermolabile agents it is to be understood that in some embodiments, they may be used with more stable agents including traditional small molecule therapeutics. Many therapeutic small molecules have been developed and may be used in accordance with the present disclosure. As used herein, the term "small molecule therapeutic" refers to a non-polymeric therapeutic molecule that may contain several carbon-carbon bonds and have a molecular weight of less than about 1500 Da (e.g., less than about 1000 Da, less than about 500 Da or less than about 200 Da). A small molecule therapeutic can be synthesized in a laboratory (e.g., by combinatorial synthesis, using an engineered microorganism, etc.) or can be found in nature (e.g., a natural product). In general, a small molecule therapeutic may alter, inhibit, activate, or otherwise affect a biological event. For example, small molecule therapeutics may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary small molecules suitable for use in the methods of the present disclosure may be found in *Pharmaceutical Substances: Syntheses, Patents, Applications*, Edited by Axel Kleemann and Jurgen Engel, Thieme Medical Publishing, 1999; *Merck Index: An Encyclopedia of Chemicals, Drugs, and Biologicals*, Edited by Susan Budavari et al., CRC Press, 1996, and the *United States Pharmacopeia-25/National formulary-20*, published by the United States Pharmacopeial Convention, Inc., 2001. Preferably, though not necessarily, the small molecule is one that has already been deemed safe and effective for use by the appropriate governmental agency or body. For example, drugs for human use listed by the FDA under 21 C.F.R. §§ 330.5, 331 through 361, and 440 through 460 and drugs for veterinary use listed by the FDA under 21 C.F.R. §§ 500 through 589, are all considered acceptable for use in accordance with the methods of the present disclosure.

Exemplary Therapeutic Agents

Table 3 provides a non-limiting list of additional exemplary agents that could be used in accordance with the present disclosure.

TABLE 3

| Substance | Reference Drug |
| --- | --- |
| Urokinase | Abbokinase ® |
| interferon gamma-1b | Actimmune ® |
| alteplase | Activase ®/Cathflo ® |
| antihemophilic factor | Advate |
| human albumin | Albutein ® |
| laronidase | Aldurazyme ® |
| interferon alfa-n3 | Alferon N ® |
| human antihemophilic factor | Alphanate ® |
| virus-filtered human coagulation factor IX | AlphaNine ® SD |
| alefacept | Amevive ® |
| bivalirudin | Angiomax ® |
| darbepoetin alfa | Aranesp ™ |
| bevacizumab | Avastin ™ |
| interferon beta-1a | Avonex ® |
| coagulation factor IX | BeneFix ™ |
| interferon beta-1b | Betaseron ® |
| tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase | Ceredase ® |
| imiglucerase | Cerezyme ® |
| Peginterferon alfa2a | Copasys Copegus ® |
| crotalidae polyvalent immune Fab | CroFab ™ |
| digoxin immune Fab | DigiFab ™ |
| rasburicase | Elitek ® |
| Asparaginase | Elspar ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| factor XIII | Hemofil ® |
| Trastuzumab | Herceptin ® |
| insulin | Humalog ® |
| antihemophilic factor/von Willebrand factor complex-human | Humate-P ® |
| somatotropin | Humatrope ® |
| adalimumab | Humira ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| palifermin | Kepivance |
| anakinra | Kineret ™ |
| antihemophilic factor | Kogenate ®FS |
| insulin glargine | Lantus ® |
| granulocyte macrophage colony-stimulating factor | Leukine ® |
| lutropin alfa, for injection | Luveris |
| ranibizumab | Lucentis ® |
| Botulinum Toxin Type B | Myobloc ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ |
| somatropin | Norditropin ®/Norditropin Nordiflex ® |
| insulin; zinc suspension | Novolin L ® |
| insulin; isophane suspension | Novolin N ® |
| insulin, regular | Novolin R ® |
| insulin | Novolin ® |
| coagulation factor VIIa | NovoSeven ® |
| somatropin | Nutropin ® |
| immunoglobulin intravenous | Octagam ® |
| pegylated-L-asparaginase | Oncaspar ® |
| Denileukin diftitox | Ontak ® |
| abatacept | Orencia ™ |
| muromomab-CD3 | Orthoclone OKT3 ® |
| human chorionic gonadotropin | Ovidrel ® |
| pegylated interferon alfa-2a | Pegasys ® |
| pegylated interferon alfa-2b | PEG-Intron ™ |
| abarelix | Plenaxis ™ |
| epoietin alfa | Procrit ® |
| aldesleukin | Proleukin, IL-2 ® |
| somatrem | Protropin ® |
| Capromab Pendetide | ProstaScint ® |
| dornase alfa | Pulmozyme ® |
| efalizumab | Raptiva ™ |
| interferon beta-1a | Rebif ® |
| antihemophilic factor | Recombinate ® |
| rAHF/ntihemophilic factor | ReFacto ® |
| lepirudin | Refludan ® |
| Becaplermin] | Regranex ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| Collagenase | Santyl ® |
| synthetic porcine secretin | SecreFlo ™ |
| basiliximab | Simulect ® |
| eculizumab | Soliris ® |
| pegvisomant | Somavert ® |
| palivizumab | Synagis ™ |
| Streptokinase | Streptase ® |
| thyrotropin alfa | Thyrogen ® |
| tenecteplase | TNKase ™ |
| natalizumab | Tysabri ® |
| Nofetumomab | Verluma ® |
| interferon alfa-n1 | Wellferon ® |
| drotrecogin alfa | Xigris ™ |
| omalizumab | Xolair ® |
| daclizumab | Zenapax ® |
| ibritumomab tiuxetan | Zevalin ™ |
| somatotropin | Zorbtive ™ (Serostim ®) |

II. Methods of Preparing Compositions

In another aspect, the present disclosure provides methods for preparing compositions including the aforementioned compositions. The specific method used may depend on the nature of the therapeutic agent, the nature of the lipid component, whether vesicles will be formed and whether these vesicles will be formed in the presence or absence of the therapeutic agent.

Compositions with Pre-Formed Vesicles

In the case of compositions that comprise pre-formed vesicles, the vesicles may be prepared in accordance with any known method and then combined with the therapeutic agent to produce a composition. For example, an exemplary technique is the rotary film evaporation method, in which a film of the vesicle-forming lipids is prepared by rotary evaporation from an organic solvent, e.g., a hydrocarbon or chlorinated hydrocarbon solvent such as chloroform, e.g., see Russell and Alexander, *J. Immunol.* 140:1274, 1988. The resulting thin film is then rehydrated in bicarbonate buffer to produce the vesicles.

Another method involves hydration in the presence of shearing forces. An apparatus that can be used to apply such shearing forces is a well known, suitable equipment (see, e.g., PCT Publication No. WO88/06882). Sonication and ultra-sonication are also effective means to form the vesicles or to alter their particle size.

Another method for the production of vesicles is that disclosed by Collins et al., *J. Pharm. Pharmacol.* 42:53, 1990. This method involves melting a mixture of the vesicle-forming lipids and hydrating with vigorous mixing in the presence of aqueous buffer.

It is to be understood that other methods, including other melt methods and spray injection methods that are described below may also be used to prepare pre-formed vesicles.

Other Compositions

When vesicles are formed in the presence of the therapeutic agent these are preferably (but not necessarily) prepared by one of the following melt or spray injection methods. Compositions that do not necessarily contain vesicles (e.g., compositions that are prepared using lipid components that consist of a non-ionic surfactant such as MPG or a non-ionic surfactant and a steroid such as MPG/cholesterol) may also be prepared in this manner even though they may not necessarily form vesicles. As discussed elsewhere, these methods avoid exposing the therapeutic agent to organic solvents and high temperatures. Without wishing to be limited to any theory, these methods are therefore thought to minimize any damage to the therapeutic agent (and hence loss in potency) that might result from other formulation methods.

Melt Method—Standard

In some embodiments, the present disclosure provides methods that involve melting the lipid(s) of the lipid component and then mixing them with the therapeutic agent. In some embodiments these methods include steps of providing a molten mixture of the one or more lipids and then adding an aqueous solution comprising the therapeutic agent to the molten mixture (standard melt method). In some embodiments the lipids form into vesicles when added to the aqueous solution.

It is to be understood that a molten mixture of one or more lipids may be obtained in any manner, e.g., lipid(s) are melted to form a molten mixture. In some embodiments, lipid(s) are melted at a temperature range between 120° C. and 150° C. (e.g., between 120° C. and 125° C., between 120° C. and 130° C., between 120° C. and 140° C., between 130° C. and 140° C., between 135° C. and 145° C., or between 140° C. and 145° C.).

In some embodiments, the mixture produced by adding the antigen solution to the molten mixture of lipid(s) is placed under temperature-controlled conditions of less than 60° C., e.g., less than 55° C., less than 50° C., less than 45° C., less than 40° C., less than 35° C., less than 30° C., less than 25° C. or even less than 20° C. In some embodiments, the molten mixture lipid(s) may be placed under the temperature-controlled conditions (e.g., using a water bath) just before the antigen solution is added. Alternatively, the antigen solution may be added to the molten mixture of lipid(s) and the resulting mixture can then be placed under temperature-controlled conditions. In some embodiments, the mixture produced by adding the antigen solution to the molten mixture of lipid(s) is placed under temperature-controlled conditions in the range of 20-60° C., e.g., 20-50° C., 20-40° C., 20-30° C., 30-60° C., 30-50° C., 30-40° C., 40-60° C., 40-50° C., or 50-60° C. It is to be understood that terms "temperature-controlled conditions" does not require the temperature to be fixed at a particular temperature but simply that the temperature remain within a range (e.g., ±1° C., ±2° C., ±5° C., ±10° C., etc. from some value) or that the temperature remain below or above a particular temperature.

In some embodiments, the aqueous solution comprising an antigen is at a temperature of less than 50° C. when added to the mixture of molten lipid(s), e.g., less than 45° C., less than 40° C., less than 35° C., less than 30° C., less than 25° C. or even less than 20° C. In some embodiments, the aqueous solution comprising an antigen is a temperature in the range of 20-60° C., e.g., 20-50° C., 20-40° C., 20-30° C., 30-60° C., 30-50° C., 30-40° C., 40-60° C., 40-50° C., or 50-60° C. when added to the mixture of molten lipid(s). In some embodiments, the aqueous solution comprising an antigen is placed under temperature-control before being added to the mixture of molten lipid(s).

In some embodiments, the molten mixture of lipid(s) is at a temperature that is no more than 50° C. above its melting point when the antigen solution is added. In some embodiments, the molten mixture of lipid(s) is at a temperature that is no more than 45° C., 40° C., 35° C., 30° C., 25° C., 20° C., 10° C., or 5° C. above its melting point when the antigen solution is added. In some embodiments, the molten mixture of lipid(s) is at a temperature that is no more than 5-50° C., e.g., 5-40° C., 5-30° C., 5-20° C., 5-10° C., 10-50° C., 10-40° C., 10-30° C., or 10-20° C. above its melting point when the antigen solution is added. For example, in some embodiments, the molten mixture of lipid(s) is at a temperature of less than 110° C., less than 100° C., less than 90° C., or less than 80° C. when the antigen solution is added.

Melt Method—Inverted

In some embodiments, the present disclosure provides methods that involve melting the lipid(s) of the lipid component and then adding the mixture of molten lipid(s) to the aqueous solution comprising a therapeutic agent (inverted melt method). In some embodiments the lipids form into vesicles when added to the aqueous solution.

In some embodiments, the aqueous solution comprising a therapeutic agent is at a temperature of less than 50° C. when the mixture of molten lipids is added, e.g., less than 45° C., less than 40° C., less than 35° C., less than 30° C., less than 25° C. or even less than 20° C. In some embodiments, the aqueous solution comprising a prophylactic and/or therapeutic agent is a temperature in the range of 20-60° C., e.g., 20-50° C., 20-40° C., 20-30° C., 30-60° C., 30-50° C., 30-40° C., 40-60° C., 40-50° C., or 50-60° C. when the mixture of molten lipid(s) is added. In some embodiments, the aqueous solution comprising a therapeutic agent is under temperature-control.

In some embodiments, the molten mixture of lipid(s) is at a temperature in the range between 120° C. and 150° C. (e.g., between 120° C. and 125° C., between 120° C. and 130° C., between 120° C. and 140° C., between 130° C. and 140° C., between 135° C. and 145° C., or between 140° C. and 145° C.) when added to the aqueous solution.

In some embodiments, the molten mixture of lipid(s) is at a temperature that is no more than 50° C. above its melting point when added to the aqueous solution. In some embodiments, the molten mixture of lipid(s) is at a temperature that is no more than 45° C., 40° C., 35° C., 30° C., 25° C., 20° C., 10° C., or 5° C. above its melting point when added to the aqueous solution. In some embodiments, the molten mixture of lipid(s) is at a temperature that is no more than 5-50° C., e.g., 5-40° C., 5-30° C., 5-20° C., 5-10° C., 10-50° C., 10-40° C., 10-30° C., or 10-20° C. above its melting point when added to the aqueous solution. For example, in some embodiments, the molten mixture of lipid(s) is at a temperature of less than 120° C., less than 110° C., less than 100° C., or less than 90° C., when added to the aqueous solution.

Solvent Injection Methods

In some embodiments, compositions may be prepared using a solvent injection method. For example, in some embodiments, the methods may involve providing a solution of one or more lipids and adding the solution of lipids to an aqueous solution comprising therapeutic agent by injection.

Solvent injection methods may offer some advantages over other preparation methods, e.g., those methods involving high temperature or pressure methods, since the lipid(s) may be dissolved in organic solutions under temperature controlled conditions. Furthermore, high pressure homogenization can be avoided using solvent injection methods.

In some embodiments, the mixture produced by injecting the solution of one or more lipids into the aqueous solution comprising a therapeutic agent is placed under temperature-controlled conditions of less than 55° C., e.g., less than 50° C., less than 45° C., less than 40° C., less than 35° C., less than 30° C., less than 25° C. or even less than 20° C. In some embodiments, the mixture produced by injecting the solution of one or more lipids into the aqueous solution comprising a therapeutic agent is placed under temperature-controlled conditions in the range of 20-55° C., e.g., 20-50° C., 20-40° C., 20-30° C., 30-55° C., 30-50° C., 30-40° C., 40-55° C., 40-50° C., or 50-55° C.

In some embodiments, the aqueous solution comprising a prophylactic therapeutic agent is at a temperature of less than 50° C. prior to injection of the solution of one or more lipids, e.g., less than 45° C., less than 40° C., less than 35° C., less than 30° C., less than 25° C. or even less than 20° C. In some embodiments, the aqueous solution comprising a therapeutic agent is a temperature in the range of 20-60° C., e.g., 20-50° C., 20-40° C., 20-30° C., 30-60° C., 30-50° C., 30-40° C., 30-35° C., 40-60° C., or 40-50° C. prior to injection of the solution of one or more lipids. In some embodiments, the aqueous solution comprising a therapeutic agent is placed under temperature-control prior to injection of the solution of one or more lipids.

In some embodiments, the solution of one or more lipids is at a temperature of less than 90° C. when it is injected into the aqueous solution comprising a therapeutic agent, e.g., less than 80° C., less than 70° C., less than 65° C., less than 60° C., or less than 55° C. In some embodiments, the solution of one or more lipids is at a temperature in the range of 50-90° C. when it is injected into the aqueous solution comprising a therapeutic agent, e.g., 50-80° C., 50-70° C., 50-65° C., 50-60° C., 50-55° C., 55-80° C., 55-70° C., 55-65° C., or 55-60° C.

Various solvent injection methods have been disclosed and can be adapted in accordance with the present disclosure. For example, solvent injection methods in which lipids were dissolved in diethyl ether are discussed in Syan et al. (Nanoparticle vesicular systems: A versatile tool for drug delivery, J. Chemical and Pharmaceutical Research 2(2): 496, 2010). In another example, solvent injection methods in which lipids were dissolved in ethanol are discussed in Wagner et al. (Liposome Technology for Industrial Purposes, J. Drug Delivery; Volume 2011, Article ID 591325). In a further example, tert-butyl alcohol was used to dissolve lipids as described by Wang et al. (Colloids and Surfaces V: Biointerfaces 79:254, 2010). See also the methods in Schubert M. A. et al. (European Journal of Pharmaceutics and Biopharmaceutics 55:125-131, 2003).

In some embodiments, the lipid(s) are dissolved in an organic solvent. In some embodiments, the solvent is an ether solvent, e.g., diethyl ether. In some embodiments, the solvent is a polar-protic water-miscible organic solvent. Protic solvents are solvents that contain dissociable protons (e.g., a hydrogen atom bound to an oxygen as in a hydroxyl group or a nitrogen as in an amine group). In some embodiments, the polar-protic water-miscible organic solvent is an aliphatic alcohol having 2-5 carbon atoms (e.g., 2 carbon atoms, 3 carbon atoms, 4 carbon atoms, or 5 carbon atoms). In some embodiments, the solvent is tert-butanol. In some embodiments, the solvent is ethanol.

In some embodiments, the one or more lipids are dissolved in a polar-protic water-miscible organic solvent without any co-solvents present. In some embodiments, the one or more lipids are dissolved in a polar-protic water-miscible organic solvent with one or more co-solvents present. In some embodiments, one or more of the co-solvents are also polar-protic water-miscible organic solvents. In some embodiments, the polar-protic water-miscible organic solvent makes up at least 70% v/v of the solvent system, e.g., at least 75%, 80%, 90%, 95% or 99%. In some embodiments, the one or more lipids are dissolved in a water-free solvent system. In some embodiments, the one or more lipids are dissolved in a solvent system that includes an amount of water such that vesicles do not form. In some embodiments, the one or more lipids are dissolved in a solvent system that includes less than 5% v/v water, e.g., less than 4%, 3%, 2%, 1%, 0.5%, or 0.1%.

Lyophilization

In some embodiments, a composition of the present disclosure may be lyophilized for future use and subsequently hydrated prior to use.

Lyophilization involves freezing the composition and then reducing the surrounding pressure (and optionally heating the preparation) to allow the frozen solvent(s) to sublime directly from the solid phase to gas (i.e., drying phase). In some embodiments, the drying phase is divided into primary and secondary drying phases.

The freezing phase can be done by placing the composition in a container (e.g., a flask, eppendorf tube, etc.) and optionally rotating the container in a bath which is cooled by mechanical refrigeration (e.g., using dry ice and methanol, liquid nitrogen, etc.). In some embodiments, the freezing step involves cooling the composition to a temperature that is below the eutectic point of the composition. Since the eutectic point occurs at the lowest temperature where the solid and liquid phase of the composition can coexist, maintaining the material at a temperature below this point ensures that sublimation rather than evaporation will occur in subsequent steps.

The drying phase (or the primary drying phase when two drying phases are used) involves reducing the pressure and optionally heating the preparation to a point where the solvent(s) can sublimate. This drying phase typically removes the majority of the solvent(s) from the composition. It will be appreciated that the freezing and drying phases are not necessarily distinct phases but can be combined in any manner. For example, in some embodiments, the freezing and drying phases may overlap.

A secondary drying phase can optionally be used to remove residual solvent(s) that was adsorbed during the freezing phase. Without wishing to be bound to any theory, this phase involves raising the temperature to break any physico-chemical interactions that have formed between the solvent molecules and the frozen preparation. Once the drying phase is complete, the vacuum can be broken with an inert gas (e.g., nitrogen or helium) before the lyophilized product is optionally sealed.

In some embodiments, the lyophilized product is substantially free of organic solvent(s).

Excipients such as sucrose, amino acids or proteins such as gelatin or serum albumin may be used to further protect the therapeutic agent during the drying process and storage. In some embodiments, a lyoprotectant may be used to protect the therapeutic agent during lyophilization. Exemplary lyoprotectants include sucrose, trehalose, polyethylene glycol (PEG), dimethyl-succinate buffer (DMS), bovine serum albumin (BSA), mannitol, sorbitol, and dextran. Any suitable amount and/or combination of lyoprotectant(s) may be used to protect the antigen. For example, as demonstrated in U.S. Pat. No. 6,290,967, the dual presence of a disaccharide (e.g., sucrose) and a 6-carbon polyhydric alcohol (e.g., a sorbitol) enhanced the stability of a vaccine composition compared to control compositions. Sucrose was added in an amount ranging from 10 to 70 grams per liter of vaccine, and sorbitol was added in an amount ranging from about 15 to 90 grams per liter of vaccine.

Rehydration

Once a composition has been lyophilized (and optionally stored), the methods of the present disclosure may include a step of rehydrating the lyophilized product. In some embodiments, this is achieved by mixing the lyophilized product with an aqueous solution.

In some embodiments, the aqueous solution includes a buffer. The buffer used will typically depend on the nature of the therapeutic agent. For example, without limitation, a PCB buffer, an $Na_2HPO_4/NaH_2PO_4$ buffer, a PBS buffer, a bicine buffer, a Tris buffer, a HEPES buffer, a MOPS buffer, etc. may be used. PCB buffer is produced by mixing sodium propionate, sodium cacodylate, and bis-Tris propane in the molar ratios 2:1:2. Varying the amount of HCl added enables buffering over a pH range from 4-9. In some embodiments, a carbonate buffer may be used.

In some embodiments, a composition may be lyophilized for future use and subsequently hydrated (e.g., with sterile water or an aqueous buffer) prior to use. In some embodiments, a composition may be stored at −80° C. prior to lyophilization.

In some embodiments, the rehydrated composition exhibits substantially the same potency as the composition prior to lyophilization.

In some embodiments, the rehydrated composition exhibits at least about 50% of the potency as the composition prior to lyophilization (e.g., at least about 55%, 60%, 65%, 70%, 75%, 80%, 85%, 90%, 95% or 99%). In some embodiments, the level of potency is based on measurements of $IC_{50}$ or $EC_{50}$ (or some other measure of potency, e.g., $TCID_{50}$ based on an in vitro microtitration assay in the case of an MMR vaccine based composition). In some embodiments, the level of potency is based on a plaque assay measurement.

In some embodiments, the rehydrated composition exhibits at least 1.5 fold greater potency as compared to an otherwise equivalent composition that was formulated without the lipid component (e.g., at least about 2 fold, 2.5 fold, 3 fold, 3.5 fold, 4 fold or 5 fold). In some embodiments, the level of potency is based on measurements of $IC_{50}$ or $EC_{50}$ (or some other measure of potency, e.g., $TCID_{50}$ based on an in vitro microtitration assay in the case of an MMR vaccine based composition). In some embodiments, the level of potency is based on a plaque assay measurement.

Storage

In some embodiments, the lyophilized composition may be stored for a period of time (e.g., days, weeks or months) prior to rehydration and administration to a subject in need thereof. In some embodiments, the lyophilized composition is exposed to temperatures in excess of 8° C. during storage (e.g., temperatures in excess of 10° C., 15° C., 20° C., 25° C., 30° C., 35° C., or 40° C., temperatures in the range of 10° C. to 40° C., temperatures in the range of 20° C. to 40° C., temperatures in the range of 30° C. to 40° C., temperatures in the range of 10° C. to 30° C., temperatures in the range of 20° C. to 30° C., room temperature, etc.). In some embodiments, the lyophilized composition is stored under conditions that are not temperature controlled.

In some embodiments, the lyophilized compositions are thermostable in that the potency of the composition remains substantially unchanged during storage despite being exposed to temperatures in excess of 8° C. (e.g., temperatures in excess of 10° C., 15° C., 20° C., 25° C., 30° C., 35° C., or 40° C., temperatures in the range of 10° C. to 40° C., temperatures in the range of 20° C. to 40° C., temperatures in the range of 30° C. to 40° C., temperatures in the range of 10° C. to 30° C., temperatures in the range of 20° C. to 30° C., 37° C., room temperature, etc.) for a period of 1 to 6 months (e.g., 1, 2, 3, 4, 5 or 6 months, 12 weeks, etc.).

In some embodiments, storage of the lyophilized composition at these elevated temperatures destroys less than 20% of the potency of the composition (e.g., less than 15%, less than 10%, less than 5%, less than 1%) as measured in a potency assay and as compared to an equivalent lyophilized composition that was stored between 2 and 8° C. for the same time period.

In some embodiments, the potency of the composition post-storage is at least 1.5 fold greater than in an otherwise equivalent lyophilized composition that was stored under the same elevated temperatures but that was formulated without the lipid component (e.g., at least about 2 fold, 2.5 fold, 3 fold, 3.5 fold, 4 fold or 5 fold). In some embodiments, the level of potency is based on measurements of $IC_{50}$ or $EC_{50}$ (or some other measure of potency, e.g., $TCID_{50}$ based on an in vitro microtitration assay in the case of an MMR vaccine based composition). In some embodiments, the level of potency is based on a plaque assay measurement.

In some embodiments, one or more of these potency results are obtained when the lyophilized composition is stored at 25° C. for 1, 2, 3, 4, 5 or 6 months. In some embodiments, these results are obtained when the lyophilized composition is stored at 15° C., 20° C., 30° C., 35° C., 37° C. or 40° C. for 1 month. In some embodiments, these results are obtained when the lyophilized composition is stored at 15° C., 20° C., 30° C., 35° C., 37° C. or 40° C. for 2 months. In some embodiments, these results are obtained when the lyophilized composition is stored at 15° C., 20° C., 30° C., 35° C., 37° C. or 40° C. for 3 months (or 12 weeks). In some embodiments, these results are obtained when the lyophilized composition is stored at 15° C., 20° C., 30° C., 35° C., 37° C. or 40° C. for 4 months. In some embodiments, these results are obtained when the lyophilized composition is stored at 15° C., 20° C., 30° C., 35° C., 37° C. or 40° C. for 5 months. In some embodiments, these results are obtained when the lyophilized composition is stored at 15° C., 20° C., 30° C., 35° C., 37° C. or 40° C. for 6 months. In some embodiments these temperatures may be allowed to vary within a range, e.g., ±2° C.

III. Dosage and Administration

The compositions and methods of this disclosure are useful for treating humans including adults and children. In general, however, compositions and methods of the present disclosure may be used with any animal. In some embodiments, compositions and methods herein may be used for veterinary applications, e.g., canine and feline applications.

If desired, compositions and methods herein may also be used with farm animals, such as ovine, avian, bovine, porcine and equine breeds.

Compositions described herein will generally be administered in such amounts and for such a time as is necessary or sufficient to induce a therapeutic response (e.g., a therapeutically effective amount). Dosing regimens may consist of a single dose or a plurality of doses over a period of time. The exact amount of a composition to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection.

In some embodiments, the dose of viral antigen in an immunogenic composition is sufficient to yield $TCID_{50}$ values that are comparable to those in a licensed vaccine. For example, the licensed M-M-R-II® vaccine includes at least 1000 $TCID_{50}$ measles virus, at least 5000 $TCID_{50}$ mumps virus and at least 1000 $TCID_{50}$ rubella virus. $TCID_{50}$ (50% tissue culture infectious dose) quantifies the amount of virus required to infect 50% of inoculated tissue culture cells. Typically, $TCID_{50}$ values are measured by plating host cells (e.g., Vero cells) and adding serial dilutions of the viral antigen. After incubation, the percentage of infected cells is manually observed and recorded for each virus dilution, and results are used to mathematically calculate a $TCID_{50}$ value, e.g., according to the Behrens-Kärber method (Kärber, *Arch Exp Pathol Pharmakol* 162:480-483, 1931).

In some embodiments, the therapeutic agent is taken from a licensed human product (e.g., a drug product or vaccine) and the composition is administered to a human at a dose that is less than the standard human dose (e.g., in the range of 10-90%, 10-80%, 10-70%, 10-60%, 10-50%, 10-40%, 10-30%, 10-20%, 20-90%, 20-80%, 20-70%, 20-60%, 20-50%, 20-40%, 20-30%, 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, or 80-90% of the standard human dose).

In some embodiments the composition is administered as a single dose. In some embodiments the composition is administered as more than one dose (e.g., 1-3 doses that are separated by 1-12 months).

In some embodiments, the compositions may be formulated for delivery parenterally, e.g., by injection. In such embodiments, administration may be, for example, intravenous, intramuscular, intradermal, or subcutaneous, or via by infusion or needleless injection techniques. In some embodiments, the compositions may be formulated for intramuscular delivery. In some embodiments, the compositions may be formulated for subcutaneous delivery. For such parenteral administration, the compositions may be prepared and maintained in conventional lyophilized compositions and reconstituted prior to administration with a pharmaceutically acceptable saline solution, such as a 0.9% saline solution. The pH of the injectable composition can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable compositions can be sterilized, for example, by filtration through a bacterial-retaining filter, or by incorporating sterilizing agents in the form of sterile solid compositions which can be dissolved or dispersed in sterile water or other sterile injectable medium prior to use.

EXAMPLES

The following examples describe some exemplary modes of making and practicing certain compositions that are described herein. It should be understood that these examples are for illustrative purposes only and are not meant to limit the scope of the compositions and methods described herein.

Example 1

Two-Step Inverted Melt Method

This example describes a two-step inverted melt method that was used to prepare certain compositions (including compositions in which vesicles were formed in the presence of a viral antigen).

In Step 1, a 5:4:1 molar ratio of the following lipids: 1-monopalmitoyl glycerol (MPG), cholesterol (CHO) and dicetyl phosphate (DCP) was placed in a flat bottom 50 ml glass beaker, ensuring none of the powder stuck to the side of the glass beaker. The lipids were melted in a heated oil bath at about 120° C. for 10 minutes, with occasional swirling in the glass beaker covered with aluminum foil.

At this stage, a stock solution of M-M-R-II® vaccine (measles, mumps and rubella virus vaccine, live attenuated, Merck Frosst Std.) was pre-incubated for 5 minutes at about 30° C. in a heated water bath. In Step 2, the resulting M-M-R-II® vaccine stock solution was homogenized at an appropriate speed (e.g., at 8,000 rpm), the molten lipid mixture was added into the homogenizing M-M-R-II® vaccine stock solution, and homogenization was continued for a further 30 seconds at about 30° C. The resulting homogenate was shaken for 30 minutes at 220 rpm and about 30° C. An equivalent volume of a 400 mM sucrose solution in 25 mM sodium bicarbonate buffer (pH 9.7) was added to the shaken homogenate and the homogenate was further shaken for 5 minutes at 220 rpm at about 30° C. This mixture was aliquoted and frozen at −80° C., then lyophilized and reconstituted with 0.5 ml of sterile water for injection (WFI) prior to use.

Example 2

Measles Potency Assays ($TCID_{50}$ and Plaque)

A common test method that is used to quantitate the number of infectious particles in live virus vaccines is the 50% Tissue Culture Infective Dose ($TCID_{50}$) assay. This endpoint dilution assay quantifies the amount of virus required to kill 50% of infected hosts or to produce a cytopathic effect in 50% of inoculated tissue culture cells. This assay may be more common in clinical research applications where the lethal dose of virus must be determined or if the virus does not form plaques (see discussion of alternative plaque assay below). In the context of tissue culture, host cells are plated and serial dilutions of the virus are added. After incubation, the percentage of cell death (i.e., infected cells) is manually observed and recorded for each virus dilution, and results are used to mathematically calculate a $TCID_{50}$ result. Due to distinct differences in assay methods and principles, $TCID_{50}$ and pfu/ml (plaque assay result) or other infectivity assay results are not equivalent. This method can take up to a week due to cell infectivity time.

Vero cells were used in these experiments to assess the potency of the measles viruses in the reformulated M-M-R-II® vaccines. Reformulated M-M-R-II® vaccines prepared in accordance with Example 1 were reconstituted after a period of storage (discussed below) in water for injection. Vero cells were grown to 80% confluency in 96-well plates. 100 µl of tenfold dilutions of the reformulated vaccine were added to wells starting with a ⅒ dilution and doing seven additional 10 fold serial dilutions of the reformulated M-M-R-II® vaccines in culture medium. The virus titer quantifies the amount of virus required to produce a cytopathic effect in 50% of inoculated tissue culture cells. Measles virus titer ($TCID_{50}$) was determined after reconstitution as discussed above.

As mentioned above, another common test method that is used to quantitate the number of infectious particles in live virus vaccines is the plaque assay. This test method is based on the cytopathic effect of the virus in the vaccine on a susceptible cell line and is an in vitro measure of the potency of the vaccine composition (Schalk et al., *Journal of Virological Methods* 117:179-187, 2004).

Reformulated M-M-R-II® vaccines prepared in accordance with Example 1 were reconstituted after a period of storage (e.g., as discussed above) in water for injection. Since the M-M-R-II® vaccine is a trivalent vaccine, mumps and rubella viruses in the vaccine were initially neutralized by the addition of anti-mumps and anti-rubella antiserum followed by incubation at 4° C. for one hour (the antisera were heat-inactivated at 56° C. for 30 minutes prior to addition). 100, 500, 1000, 2500 and 5000-fold serial dilutions of the reformulated M-M-R-II® vaccines in culture medium were then prepared. Vero cells were grown to 90% confluency in 6-well plates. One day before infection, culture medium was refreshed. Cells were infected with 200 µl of each dilution (12 wells per dilution). After absorption of the virus for 45 minutes at room temperature, cells received a 4 ml agar-overlay consisting of medium M199 (BioWhittaker Europe) with 4.7% inactivated fetal calf serum (Invitrogen), 0.11% $NaHCO_3$ and 0.33% agar. The plates were inverted and incubated at 36° C. and 2.5% $CO_2$. After 9 days, the agar-overlay was removed and cells are fixed in 96% ethanol for 2 minutes. Subsequently, cells were stained in carbol fuchsin and dried. Plaques were generally counted manually and results, in combination with the dilution factor used to prepare the plate, were used to calculate the number of plaque forming units per sample unit volume (pfu/ml).

The pfu/ml result represents the number of infective particles within the sample and is based on the assumption that each plaque formed is representative of one infective virus particle.

Example 3

Comparison of Viral Antigen-Containing Vesicles and Preformed Vesicles Admixed with Viral Antigen: Effect of Lipid Concentration on Thermostability and Liquid Stability This study was designed to evaluate the stabilization of non-ionic surfactant vesicles (NISVs) containing live attenuated M-M-R-II® formulated with different lipid concentrations, buffers and sucrose using the inverted melt process as described in Example 1. The study also compared formulating M-M-R-II® into vesicles versus formulating M-M-R-II® with pre-formed vesicles. The samples were stored at 5±3° C. and 37±2° C. The commercial vaccine M-M-R-II® was used as a positive control for comparison. The $TCID_{50}$ was used as an in vitro test (as described in Example 2) to determine the vaccine potency following 1, 2 and 12 weeks of storage. The results were compared to the performance of the commercial vaccine to evaluate the thermostable benefit of the reformulated samples.

A 5:4:1 molar ratio of the lipids: monopalmitoyl glycerol (MPG), cholesterol (CHO) and dicetyl phosphate (DCP) were placed in the bottom of a flat bottom glass beaker. The lipids were melted in an oil bath at 120° C.-122° C. with occasional mixing. M-M-R-II® vaccine (reconstituted with supplied diluents) was warmed at 30° C.-32° C. for 5 minutes. The M-M-R-II® vaccine solution was homogenized at 8000 rpm and the melted lipids were immediately transferred into the vaccine solution, and warmed at 30° C.-32° C. After homogenization (10 minutes for TA 8 and 9; 30 seconds for TA 1-7 and 10-12), the resulting mixture was mixed for 30 minutes at 220 rpm at 30° C.-32° C. For certain samples, an equivalent volume of 400 mM sucrose solution, optionally prepared with 25 mM of bicarbonate buffer or sterile water, was then added. The prepared sample was mixed for another 5 minutes at 220 rpm at 30° C.-32° C. For TA 4, the concentrated phosphate buffer was added to M-M-R-II® vaccine solution prior to adding melted lipid. The solution was aliquoted into 1.0 mL aliquots/vial (TA 1-4, 8, 9, 10, 11) and 0.5 mL (TA 5-7 and 12) followed by lyophilization. The lyophilized vials were stored at 5±3° C. and 37±2° C. Each vial of lyophilized samples was reconstituted with 1.0 mL of sterile water prior to Tissue Culture Infectious $Dose_{50}$ ($TCID_{50}$) analysis. The samples for this stability study are as described in the following Table 4.

TABLE 4

| | | Excipients | | | | |
|---|---|---|---|---|---|---|
| TA# | Antigen | Lipid (mg/mL) | Sucrose (mM) | Conc. Phosphate Buffer (mM) | Bicarbonate Buffer** (mM) | Fill Volume/Vial Size |
| 1 | M-R-II ® | 25 | 400 | — | 25 | 1 mL/6 cc |
| 2 | M-R-II ® | 12.5 | 400 | — | 25 | 1 mL/6 cc |
| 3 | M-R-II ® | 3.125 | 400 | — | 25 | 1 mL/6 cc |
| 4 | M-R-II ® | 12.5 | 400 | 50* | — | 1 mL/6 cc |
| 5 | M-R-II ®* | 25 | — | — | — | 0.5 mL/2 cc |
| 6 | M-R-II ® | 12.5 | — | — | — | 0.5 mL/2 cc |
| 7 | M-R-II ® | 3.125 | — | — | — | 0.5 mL/2 cc |
| 8 | M-R-II ® | 25 | 400 | Pre-formed NISV + 25* | — | 1 mL/6 cc |

TABLE 4-continued

| | | | | Excipients | | |
|---|---|---|---|---|---|---|
| TA# | Antigen | Lipid (mg/mL) | Sucrose (mM) | Conc. Phosphate Buffer (mM) | Bicarbonate Buffer** (mM) | Fill Volume/Vial Size |
| 9 | M-R-II® | 12.5 | 400 | Pre-formed NISV + 25* | — | 1 mL/6 cc |
| 10 | M-R-II® | No NISV | 400 | — | 25 | 1 mL/6 cc |
| 11 | M-R-II® | No NISV | 400 | 50* | — | 1 mL/6 cc |
| 12 | M-R-II® | No NISV | — | — | — | 0.5 mL/2 cc |
| 13 | M-R-II® | — | — | — | — | 0.5 mL/2 cc |

*Phosphate buffer was used to buffer M-R-II ® vaccine prior to lipid addition.
**25 mM Sodium Bicarbonate pH 9.7 was used to dissolve 400 mM Sucrose and added to samples prior to lyophilisation The lyophilized samples were collected from the temperature chamber. All samples were coded and stored at 4° C. before testing. The potency of measles component was determined with an in vitro microtitration assay. The TCID$_{50}$ assay estimated viable virus using a streamlined endpoint dilution assay that was analyzed statistically. Briefly, serial dilutions of these samples and the reference standard preparations were inoculated in rows of 10 wells of microtiter plates, together with Vero cells (African green monkey kidney epithelial cells; ATCC-CCL 81) used for 1, 2 and 12 week sample. The Vero cell line was initiated from the kidney of a normal adult African green monkey. The microtitre plates were inoculated with 50 µL at of Vero cells in order to obtain 4.0×10$^5$ cells/mL titer in 24 hrs at 5% CO2/37° C. (75-80% cell confluence is expected in these conditions). Each sample was reconstituted with 1000 µl of sterile distilled water, mixed for 15 seconds by hand followed with vortex for 45 seconds on medium speed (setting 5). The reconstituted samples (4 vials per time point) were transferred to the microtitre plates within 5 minutes in undiluted and diluted form (10-1 to 10-7) on a 96-well plate in quadruplicates (100 µL/well). Dilutions 10-1 to 10-7 were prepared in 24-well plates completed with 5% FBS supplemented IMDM media and 100 µL was added to individual wells in quadruplicates. Positive and negative controls were included (in house processed commercial vaccine/commercial vaccine and cells, respectively). The plates were incubated at 35° C./5% CO$_2$ for 5 days. At the end of the incubation period, the numbers of the specific viral cytopathic effect (CPE) were counted and recorded. The TCID$_{50}$ per human dose was calculated according to these criteria. TCID$_{50}$ values were used to derive the geometric mean titers for statistical analysis.

For statistical analysis of all the samples, the transformed variables were related by using Prism 5 for windows (GraphPad Software, San Diego, Calif.) software to perform two tailed unpaired t-test and detect p-value between the groups. Statistical significance is indicated by a p-value between 0.05 to 0.01 and high statistical significance is indicated by a p-value less than 0.01. TCID$_{50}$ values were manipulated if the titre was identical for all the experiments in one group, such that the titre was rounded to the fourth decimal point to avoid the software limitation for nonparametric statistical analysis.

In FIG. 1 depicts the TCID$_{50}$ assay results of the samples (TA 1, 5 and 8) formulated with 25 mg/mL lipid, process controls TA 10 and TA12 (commercial vaccines exposed to all processing steps without lipid, with and without sucrose and buffer) and commercial vaccine (M-M-R-II®, TA 13) at both 5±3° C. and 37±2° C. The container closure system and the fill volume for TA 1 (1 mL of the reformulated proposed sample in 6 cc vials) was different compared to TA 5 (0.5 mL filled into a 2 cc vial) but results obtained for TCID$_{50}$ and physicochemical characterizations (data not shown) were comparable. The potency of TA 1, 5 and 8 stored over 1, 2 and 12 weeks at 5±3° C. and 37±2° C. was higher than the limit advised by WHO (3.0 log$_{10}$) (FIG. 1). The reformulated samples with 25 mg/mL lipid did not show a loss in potency over 12 weeks when stored at higher temperature (37±2° C.) whereas the commercial vaccine potency decreased significantly (p<0.0001). The M-M-R-II® vaccine added to pre-formed NISV and formulated by the inverted melt method showed comparable TCID$_{50}$ results. It was also observed that the non-lipid containing process control TA 10 and TA 12 were not stable for more than one week when stored at higher temperature (37±2° C.) (FIG. 1, TA 10). The TA 12 did not show stability at higher temperature after one week compared to the commercial vaccine which was stable up to two weeks at 37±2° C. but showed a decrease after 12 weeks. These results demonstrate a thermostable M-M-R-II® vaccine with a lipid concentration of 25 mg/mL (with or without sucrose and buffer) at elevated temperatures. At 5±3° C., the TA 1, 5 and 8, the process controls (TA 10 and 12) and the commercial M-M-R-II® (TA 13) showed no loss in potency over 12 weeks of storage. TA 1, 5 and 8 stored at 37±2° C., maintained higher potency compared to the commercial vaccine.

Figure 2:
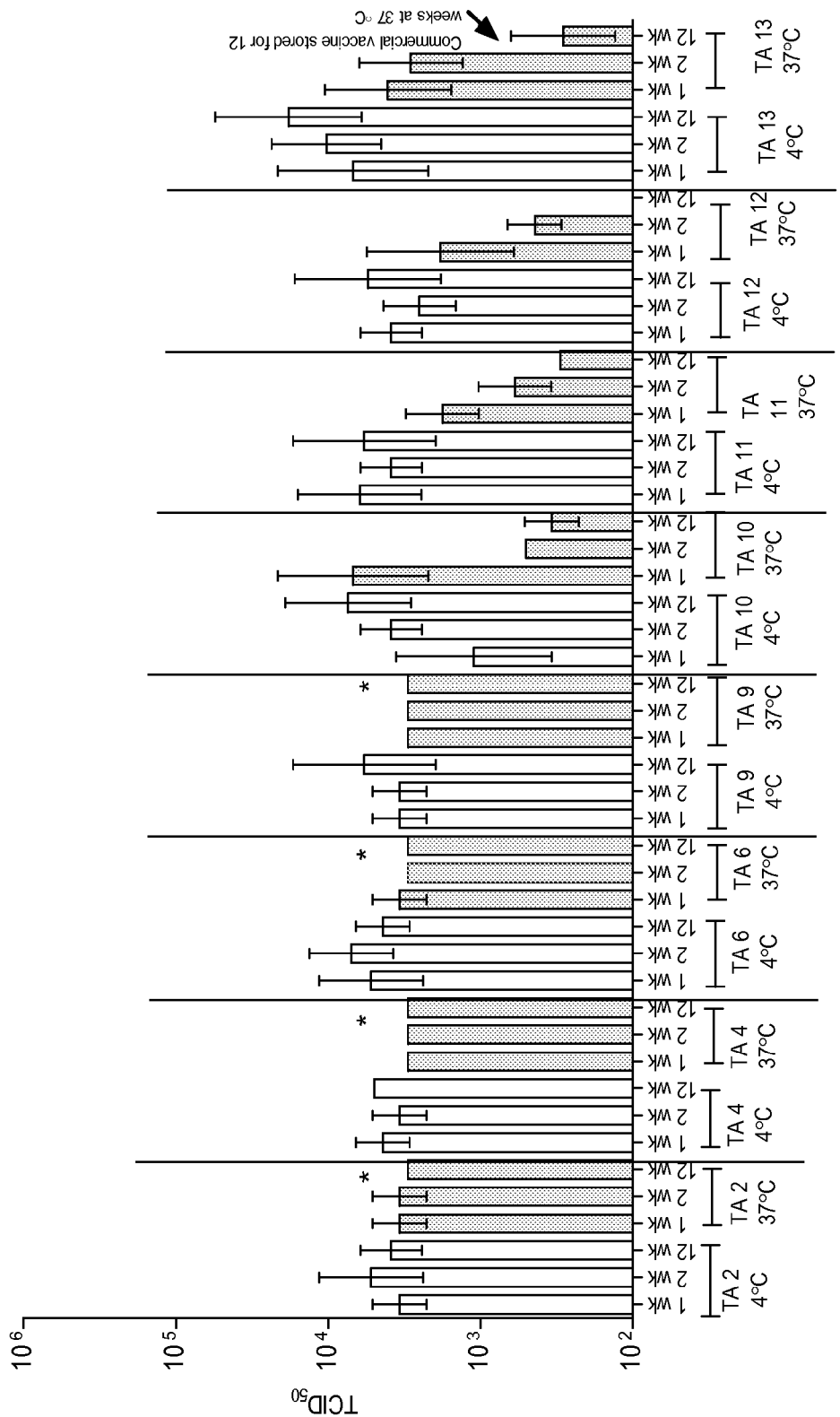
FIG. 2 shows exemplary results from a measles potency assay ($TCID_{50}$) that was performed using different reformulated M-M-R-II® vaccines (formulated with 12.5 mg/ml lipid) that had been stored at about 4° C. and about 37° C. for 1, 2 and up to 12 weeks.

In FIG. 2 is shown the TCID$_{50}$ assay results of the samples (TA 2, 4, 6 and 9) formulated with 12.5 mg/mL lipid, process control (commercial vaccines exposed to all processing steps without lipid, with and without sucrose and buffer) and commercial vaccine (M-M-R-II®) at both 5±3° C. and 37±2° C. The container closure system and the fill volume for TA 2 (1 ml of the reformulated proposed Test Article in 6 cc vials) was different compared to TA 6 (0.5 ml filled into 2 cc vials). The appearance of TA 6 was more consistent throughout the storage at higher temperature. The potency of TA 2, 4, 6 and 9 stored over 1, 2 and 12 weeks at 5±3° C. and 37±2° C. was higher than the limit advised by WHO (3.0 log$_{10}$) (FIG. 2). The reformulated samples with 12.5 mg/mL lipid showed no loss in potency over 12 weeks storage at higher temperature (37±2° C.) whereas the commercial vaccine potency significantly decreased (p<0.0001). The pre-formed NISV (TA 9) and the inverted melt method compositions (TA 2, 4 and 6) showed comparable TCID results. It was also observed that the reformulated process control samples were not stable for more than one week when stored at higher temperature (37±2° C.) (FIG. 2 for TA 10 and TA 11). TA 12 did not show a loss in potency at higher temperature after one week compared to the commercial vaccine which was stable up to two weeks at 37±2° C. These results demonstrate a thermostable M-M-R-II® vaccine with the lipid concentration of 12.5 mg/ml. At 5±3° C., the samples (TA 2, 4, 6 and 9), process control (no lipids) and the commercial vaccine showed stability up to 12 weeks. Samples formulated with NISVs (TA 2, 4, 6 and 9) stored at both temperatures (5±3° C. and 37±2° C.) maintained higher potency compared to the 2 and 12 week old commercial vaccines.

In summary, the lyophilized samples containing M-M-R-II® vaccine in NISVs (12.5 or 25.0 mg/mL of lipid) prepared by inverted melt process had no change in potency over 12 weeks storage at 5±3° C. and 37±2° C. The highest lipid concentration tested 25 mg/mL did not appear to provide any additional benefit in maintaining potency compared to samples containing lower lipid concentration (12.5 mg/mL). The lyophilized sample containing M-M-R-II® vaccine added to pre-formed NISVs had no loss in potency over 12 weeks storage at 5±3° C. and 37±2° C.

Example 4

Physical Characterization of Compositions Prepared with Different Lipid Components The main objective of this study was to investigate the use of 1, 2 dipalmitoylphosphatidyl glycerol (DPPG) as an alternative anionic surfactant to DCP in lipid-M-M-R-II® compositions prepared by the inverted melt method (as described in Example 1). The secondary objective was to investigate excluding DCP or DPPG (and also CHO) in the M-M-R-II® compositions.

A 5:4:1 molar ratio of the lipids: MPG, CHO and DCP or DPPG were placed in the bottom of a flat bottom glass beaker. The lipids were melted in an oil bath at 120° C.-122° C. (140° C. for samples with DPPG) with occasional mixing. M-M-R-II® vaccine (reconstituted with supplied diluents) was warmed at 30° C.-32° C. for 5 minutes. The M-M-R-II® vaccine solution was homogenized at 8000 rpm and the melted lipids immediately transferred into the vaccine solution, warmed at 30° C.-32° C. After 30-40 seconds of homogenization, the mixture was mixed for 30 minutes at 220 rpm at 30° C.-32° C. The solution was aliquoted into 0.5 mL/vial (2 cc lyophilization vial) followed by lyophilization. The lyophilized vials were stored at 2-8° C. after lyophilization. Each vial of lyophilized sample was reconstituted with 0.5 mL of distilled water (GIBCO) prior to analysis. TA 5, the M-M-R-110 in-process control, was prepared by putting hydrated M-M-R-II® commercial vaccine through the inverted melt process in the absence of lipids. TA 6, the commercial vaccine control remained as a lyophilized powder until analysis. The samples for this study are as described in the following Table 5.

TABLE 5

| Test Article | Antigen | Method | Lipid (mg/mL) | Excipients |
|---|---|---|---|---|
| 1 | M-M-R-II ® | Inv Melt | 12.5 | MPG/CHOL/DCP: 5/4/1 |
| 2 | M-M-R-II ® | Inv Melt | 12.5 | MPG/CHOL/DPPG: 5/4/1 |
| 3 | M-M-R-II ® | Inv Melt | 12.5 | MPG/CHOL: 5/4 only |
| 4 | M-M-R-II ® | Inv Melt | 12.5 | MPG only |
| 5 | M-M-R-II ® | — | — | Process control |
| 6 | M-M-R-II ® | — | — | Commercial control |

A number of biophysical characterizations were conducted on the various samples as described in the following paragraph. The pH of the samples was measured by standard methods. The zeta potential of the samples was analyzed using electrophoretic light scattering. The size distribution of each sample was analyzed by dynamic light scattering using the Zetasizer Nano ZS (Model No. ZEN3600). In brief, all lipid-containing samples were diluted to 50 μg/mL lipid in 0.2 μm filtered WFI. The diluted samples were vortexed rigorously before loading into the instrument. The sample refractive index was set to 1.45 and three consecutive measurements were conducted on each sample. TA 1-6 were examined at t=0, using a light microscope with a 40× objective. The samples were analyzed for residual water content using a Karl Fischer Titrator following lyophilization. Results for the biophysical characterization of the samples is presented in Table 6.

TABLE 6

| Test | TA 1 | TA 2 | TA 3 | TA 4 | TA 5 | TA 6 |
|---|---|---|---|---|---|---|
| Appearance (post-lyophilization) | Light-yellow cake | Light-yellow cake | Light-yellow cake | Light-yellow cake | Light-yellow cake | Light-yellow cake |
| pH (post-reconstitution) | 6.47 | 6.49 | 6.47 | 6.50 | 6.52 | 6.53 |
| Water Content (%)* | 3.30 | 4.74 | 6.29 | 5.06 | 6.11 | 5.69 |
| Average Zeta Potential (mV)** | −48.5 | −38.8 | −16.7 | −13.7 | −6.40 | −5.68 |
| Average Z Average (d.nm)*** | 298.3 | 442.6 | 803.1 | 707.0 | 685.6 | 879.3 |
| Average Polydispersity Index (PI) | 0.357 | 0.522 | 0.741 | 0.777 | 0.604 | 0.710 |

*Calculated based on Karl Fischer Titration of Test Articles post-lyophilization
**Hydrodynamic diameter calculated by DLS using Malvern Zetasizer Nano ZS
***Calculated by electrophoretic light scattering using Malvern Zetasizer Nano ZS The pH values for all of the samples were comparable to commercial vaccine control (TA 6). Residual moisture content for all samples ranged between 3.30-6.29%. The lowest of which was TA 1 with 5:4:1 molar lipid ratio of MPG: CHO:DCP. The highest residual moisture content was observed in TA 3 (MPG:CHO; 5:4 molar lipid ratio). Z-average and polydispersity index (PI) of TA 2 (containing MPG:CHO:DPPG) were slightly higher when compared to the TA 1 (MPG:CHO:DCP) which suggested a polydisperse system of particles in TA 2 (see Table 6). Hydrodynamic diameter and PI of TA 3 (803.1 nm; PI=0.741) and TA 4 (707.0 nm; PI=0.777) were larger than those prepared with an ionic surfactant (TA 1 and TA 2). Zeta potential values for TA 1 (−48.5 mV) and 2 (−38.8 mV) containing anionic surfactant had more negative values than those without anionic surfactants and non lipid controls (−5.68 to −16.7 mV). Microscopically, lipid vesicle particles (LPV) were observed for the samples containing surfactants (TA 1 and 2, data not shown). However, visible aggregates of lipid particles were seen in the non-surfactant containing samples (TA 3 and 4). No visible lipid particles were seen in the non lipid containing controls (TA 5 and 6). Light yellow lyophilized cakes were observed for all of the samples (see Table 6).

Example 5

Use of an Anionic Surfactant in Vesicles and Pre-Formed Vesicles with an Exemplary Therapeutic Protein The main objective of this study was to investigate the use of 1, 2 Dipalmitoylphosphatidyl Glycerol (DPPG) as an alternative anionic surfactant to DCP in NISV formulations prepared by Inverted Melt Method (as described in Example 1) with an exemplary therapeutic protein (trastuzumab, a monoclonal antibody that interferes with the HER2/neu receptor). The secondary objective was to investigate whether admixing the therapeutic protein with pre-formed anionic surfactant vesicles can impart thermostability.

A 5:4:1 molar ratio of the lipids: MPG, CHO and DPPG were placed in the bottom of a flat bottom glass beaker. The lipids were melted in an oil bath at 140° C. with occasional mixing. Dialyzed trastuzumab solution (buffer exchanged with 5% sucrose in 25 mM Tris and 25 mM of Sodium-Citrate buffer, pH 6.5) was warmed at 32° C.-35° C. for 5-10 minutes. The trastuzumab solution was homogenized at 8000 rpm and the melted lipids immediately transferred into the therapeutic protein solution, warmed at 30° C.-32° C. After 2 minutes of homogenization, the liposome mixture was mixed for 15-30 minutes at 220 rpm at 300 C-350 C in an incubator shaker. The solution was aliquoted into 0.5 mL/vial (2 cc lyophilization vial) followed by lyophilization. The lyophilized vials were stored at 2-8° C. after lyophilization. Each vial of lyophilized Test Article was reconstituted with 0.5 mL of WFI water. Pre-formed vesicles were similarly made except that the homogenization step occurs with buffer only and the trastuzumab was admixed to the pre-formed vesicles after formulation rather than during formulation. The Test Articles for this stability study are as described in the following Table 7. For the No-LPV control ("Control-4", unformulated trastuzumab), trastuzumab solution was not dialyzed and remained in a buffer of 20 mM Histidine, 7% Sucrose, 0.01% PS20, pH 6.0.

TABLE 7

| Test Article | Antigen | Method | Lipid (mg/mL) | Excipients |
| --- | --- | --- | --- | --- |
| LPV-1 | Trastuzumab | Inverted Melt Method | 12.5 | MPG/CHOL/DPPG: (5/4/1) 5% sucrose in 25 mM Tris and 25 mM of Sodium-Citrate buffer, pH 6.5 |
| LPV-2 | Trastuzumab | Pre-formed LPV | 12.5 | MPG/CHOL/DPPG: (5/4/1) |
| LPV-3 | Trastuzumab | Pre-formed LPV | 25.0 | MPG/CHOL/DPPG: (5/4/1) 5% sucrose in 25 mM Tris and 25 mM of Sodium-Citrate buffer, pH 6.5 |
| Control-4 | Trastuzumab | No-LPV control | — | Commercial control 7% sucrose in 20 mM histidine and 0.01% PS20 buffer, pH 6.0 |

Example 6

Comparison of Thermostability of an Exemplary Therapeutic Protein in Anionic Surfactant Vesicles or Admixed with Pre-Formed Vesicles The purity and potency of trastuzumab formulated in NISV's was evaluated after 8 weeks storage at two temperatures (5° C.±3° C. and 37° C.±2° C.) using a Size Exclusion Chromatography (SEC) procedure to determine percent purity and a BT-474 anti-proliferation biological potency assay. A validated potency assay for trastuzumab is the BT-474 inhibition of proliferation bioassay. This assay measures the activity of the Fab binding affinity. The principle of the trastuzumab inhibition of proliferation bioassay is that the relevant target cell line, typically BT-474 cells are prepared in cell plates using a procedure designed to optimize receptor expression. A dilution series of trastuzumab is then prepared, added to the plate and allowed to bind to the BT-474 cells for a period of time. Sample results are reported as a percent of inhibition of cell growth or as a relative potency measurement against a reference standard. The results were compared to the performance of the unformulated therapeutic protein to evaluate the thermostable benefit of the reformulations.

Figure 3:
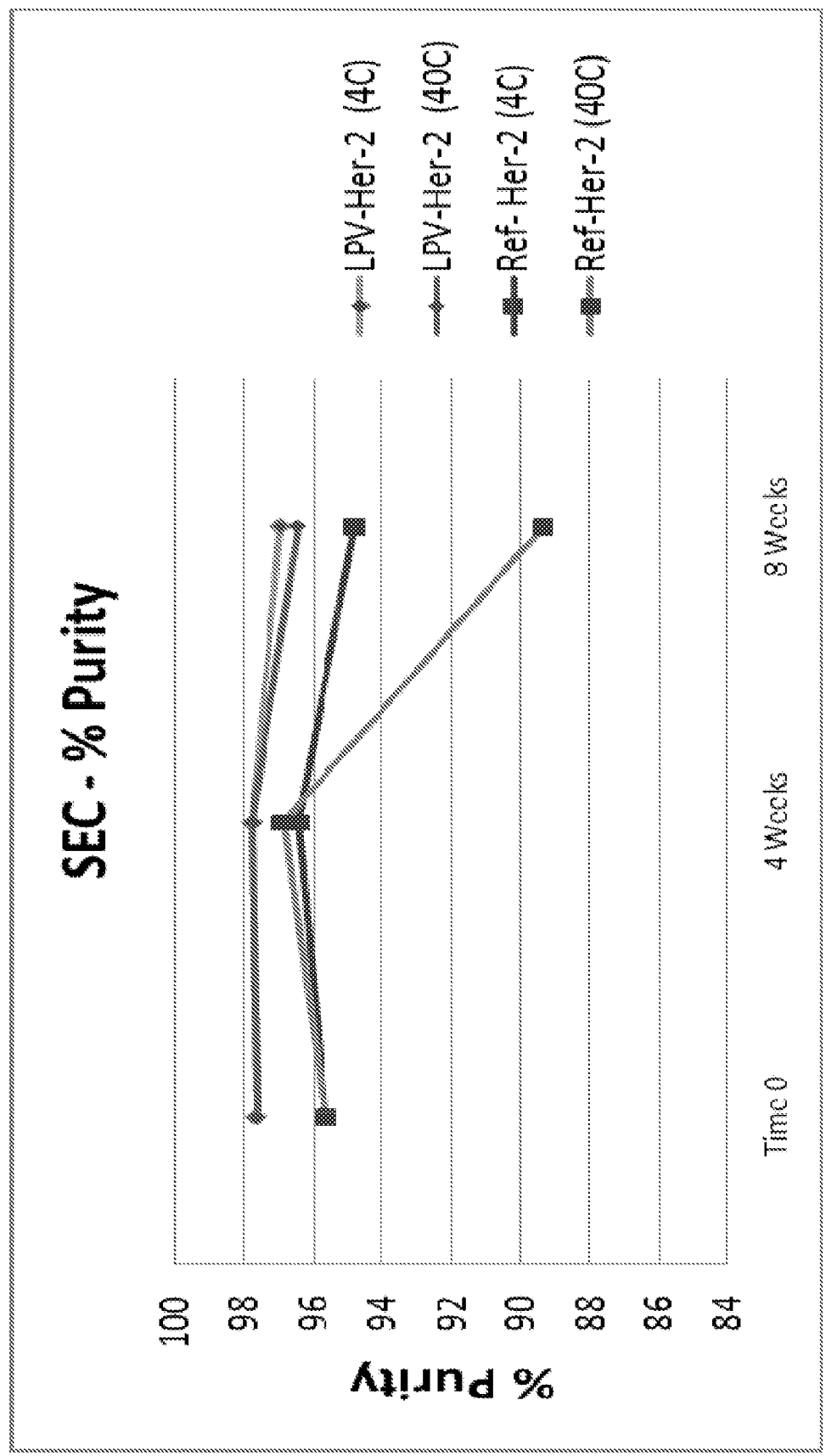
FIG. 3 shows percent purity results from Size Exclusion Chromatography that was performed using reformulated trastuzumab as an exemplary therapeutic protein (formulated with 12.5 mg/ml lipid) that had been stored at about 4° C. and about 40° C. for 4 and up to 8 weeks.

FIG. 3 shows the SEC percent purity results of the Test Article LPV-1 (trastuzumab formulated with DPPG containing vesicles) versus the no-LPV control test article (unformulated trastuzumab) for the evaluation of effect on thermostability at 8 weeks of storage at 40° C. versus 4° C. The no-LPV reference control showed a loss in % purity (measured as single major peak on SEC) when stored for 8 weeks at 40° C. versus when stored for 8 weeks at 4° C. In contrast to the no-LPV control, there were no differences in % purity observed in the lipid containing Test Article (LPV-1) stored for 8 weeks at either 4° C. or 40° C.

Figure 4:
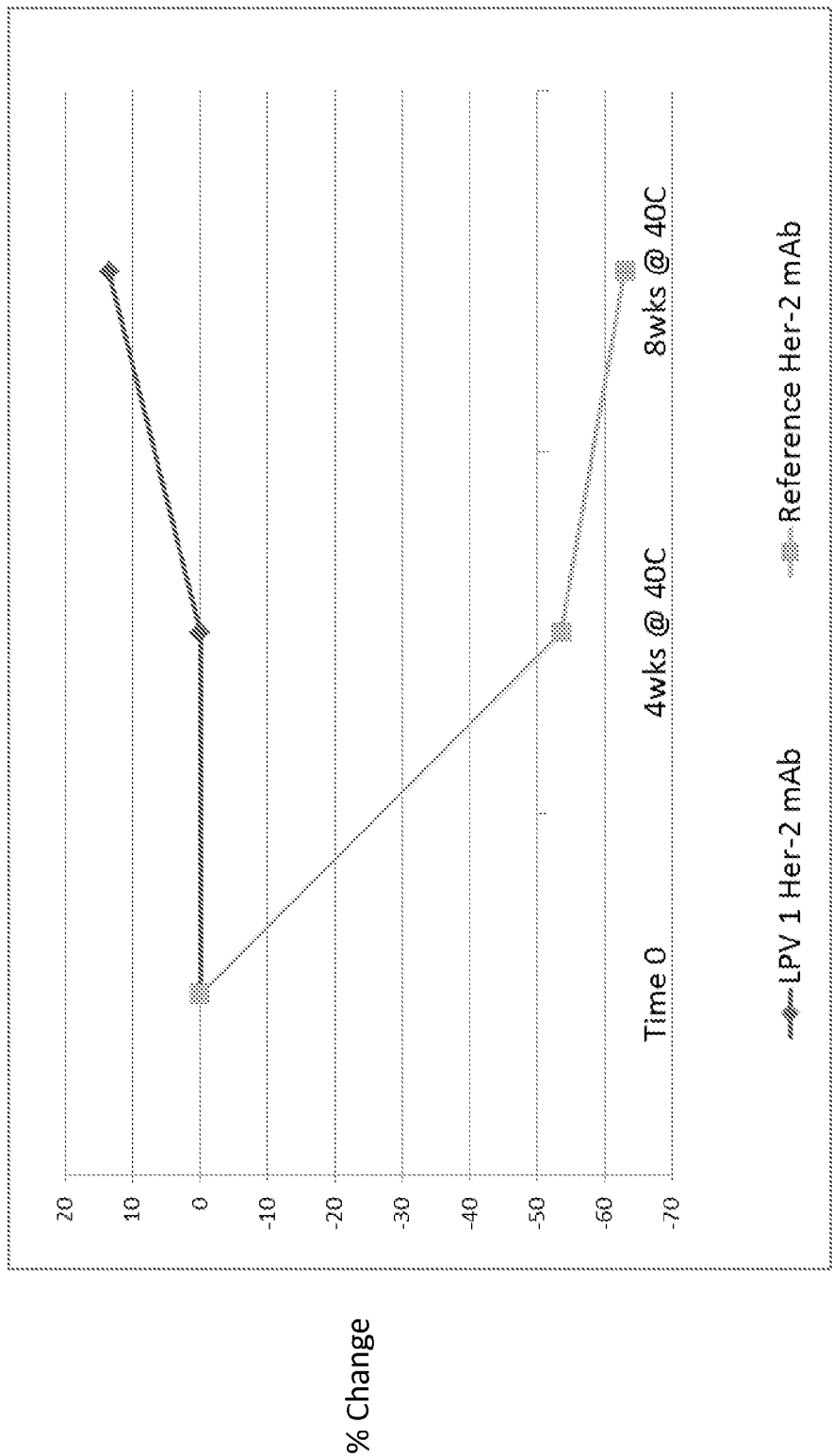
FIG. 4 shows potency results from BT-474 anti-proliferation biological potency assay that was performed using reformulated trastuzumab as an exemplary therapeutic protein (formulated with 12.5 mg/ml lipid) that had been stored at about 4° C. and about 40° C. for 4 and up to 8 weeks.

FIG. 4 shows the BT-474 anti-proliferation biological potency assay results of the Test Article LPV-1 (trastuzumab formulated with DPPG containing vesicles) versus the no-LPV control test article (unformulated trastuzumab) for the evaluation of effect on thermostability at 8 weeks of storage at 40° C. versus 4° C. The no-LPV reference control showed a loss in potency (as measured by UV detection) when stored for 8 weeks at 40° C. versus when stored for 8 weeks at 4° C. In contrast to the no-LPV control, there were no differences in % purity observed in the lipid containing Test Article (LPV-1) stored for 8 weeks at either 4° C. or 40° C. Comparable results were observed whether the therapeutic protein trastuzumab was formulated with DPPG containing vesicles or admixed to pre-formed Anionic surfactant vesicles.

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

What is claimed is:

1. A method comprising:
   preparing pre-formed vesicles comprising a lipid component that comprises a non-ionic surfactant, a steroid and an ionic amphiphile;
   admixing the pre-formed vesicles with an aqueous solution that includes a thermolabile therapeutic agent, wherein pre-formed vesicles are prepared in the absence of thermolabile therapeutic agent;
   homogenizing the resulting product to form a homogenate, wherein the homogenate does not comprise thermolabile therapeutic agent entrapped within the pre-formed vesicles; and
   lyophilizing the homogenate to form a lyophilized homogenate,
   wherein the ionic amphiphile is dicetylphosphate (DCP) or 1,2-dipalmitoylphosphatidyl glycerol (DPPG), and
   when the ionic amphiphile is DCP, the non-ionic surfactant is 1-monopalmitoyl glycerol (MPG) and the steroid is cholesterol (CHO); and
   when the ionic amphiphile is DPPG, the non-ionic surfactant is MPG and the steroid is CHO and the MPG, CHO, and DPPG are present in a ratio of 5:4:1.

2. The method of claim 1, wherein the ionic amphiphile is DCP.

3. The method of claim 1, wherein the ionic amphiphile is DPPG.

4. The method of claim 1, wherein preparing the pre-formed vesicles comprises:
   (a) melting the lipid component, and adding the molten lipid component to an aqueous solution that lacks the thermolabile therapeutic agent; or
   (b) melting the lipid component, and adding an aqueous solution that lacks the thermolabile therapeutic agent to molten lipid component.

5. The method of claim 1, wherein the thermolabile therapeutic agent comprises:
   (a) an attenuated measles virus, an attenuated mumps virus, an attenuated rubella virus, and attenuated varicella virus, or a combination thereof;
   (b) an attenuated virus selected from the group consisting of an attenuated rotavirus, an attenuated herpes zoster virus, an attenuated vaccinia virus, an attenuated yellow fever virus, and combinations thereof;
   (c) a therapeutic protein; or
   (d) a polynucleotide or polysaccharide.

6. The method of claim 1, wherein the lyophilized homogenate possesses higher stability at temperatures greater than 4 degrees Celsius when compared to a lyophilized immunogenic composition consisting of the thermolabile therapeutic agent.

7. The method of claim 5, wherein the therapeutic protein is an antibody.

8. The method of claim 5, wherein the therapeutic protein is an antibody fragment.

* * * * *